US009879057B2

(12) United States Patent
Mutharia et al.

(10) Patent No.: US 9,879,057 B2
(45) Date of Patent: Jan. 30, 2018

(54) BIOMARKERS FOR *MYCOBACTERIUM AVIUM PARATUBERCULOSIS* (MAP)

(71) Applicant: University of Guelph, Guelph (CA)

(72) Inventors: Lucy M. Mutharia, Guelph (CA); Antonio Facciuolo, Guelph (CA)

(73) Assignee: University of Guelph, Guelph, ON (CA)

( * ) Notice: Subject to any disclaimer, the term of this patent is extended or adjusted under 35 U.S.C. 154(b) by 0 days.

(21) Appl. No.: 15/024,238

(22) PCT Filed: Sep. 24, 2014

(86) PCT No.: PCT/CA2014/050914
§ 371 (c)(1),
(2) Date: Mar. 24, 2016

(87) PCT Pub. No.: WO2015/042704
PCT Pub. Date: Apr. 2, 2015

(65) Prior Publication Data
US 2016/0215028 A1 Jul. 28, 2016

Related U.S. Application Data

(60) Provisional application No. 61/881,756, filed on Sep. 24, 2013.

(51) Int. Cl.
*A61K 39/04* (2006.01)
*C07K 14/35* (2006.01)
*G01N 33/569* (2006.01)
*C07K 16/12* (2006.01)

(52) U.S. Cl.
CPC .............. *C07K 14/35* (2013.01); *A61K 39/04* (2013.01); *C07K 16/1289* (2013.01); *G01N 33/5695* (2013.01); *C07K 2317/33* (2013.01); *G01N 2333/35* (2013.01); *G01N 2469/20* (2013.01)

(58) Field of Classification Search
CPC .............................. A61K 39/04; G01N 33/53
USPC ......... 424/184.1, 185.1, 234.1, 248.1; 435/4, 435/7.1, 7.2
See application file for complete search history.

(56) References Cited

U.S. PATENT DOCUMENTS

| 7,867,704 B2 * | 1/2011 | Kapur | C12Q 1/689 |
| | | | 435/243 |
| 8,445,656 B2 | 5/2013 | Verschoor et al. | |
| 8,470,339 B2 | 6/2013 | Leroy et al. | |
| 2004/0197896 A1 | 10/2004 | Cole | |

OTHER PUBLICATIONS

Tiwari, A., et al., "Estimate of the direct production losses in Canadian dairy herds with subclinical *Mycobacterium avium* sub-species paratuberculosis infection." Can. Vet. J., 2008, 49:569-576.
United States Department of Agriculture (USDA), "Johne's disease on U.S. dairies, 1991-2007." APHIS, Info Sheet, Apr. 2008, VS National Animal Health Monitoring System, 1991-2007, No. 521.0408.
Harris, N. B., and Barletta, R.G., "*Mycobacterium avium* subsp. paratuberculosis in veterinary medicine." Clin. Microbiol. Rev., 2001, 14:489-512.
Van Roermund, H.J., et al., "Horizontal transmission of *Mycobacterium avium* subsp. paratuberculosis in cattle in an experimental setting: Calves can transmit the infection to other calves." Vet. Microbiol., 2007, 122:270-279.
Collins, M.T., et al., "Successful control of Johne's disease in nine dairy herds: Results of a six-year field trial." J. Dairy Sci., 2010, 93:1638-1643.
Wadhwa, A., et al., "Opportunities for Improved Serodiagnosis of Human Tuberculosis, Bovine Tuberculosis, and Paratuberculosis." Vet. Med. Int., 2012:674238. doi: 10.1155/2012/674238.
Collins, M.T., et al., "Consensus recommendations on diagnostic testing for the detection of paratuberculosis in rattle in the United States." J. Am. Vet. Med. Assoc., 2006, 229:1912-1919.
Sweeney, R.W., et al., "Longitudinal study of ELISA seroreactivity to *Mycobacterium avium* subsp. paratuberculosis in infected cattle and culture-negative herd mates." J. Vet. Diagn. Invest., 2006, 18:2-6.
Singh, S.V., et al., "Evaluation of an indigenous ELISA for diagnosis of Johne's disease and its comparison with commercial kits." Indian. J. Microbiol., 2007, 47:251-258.
Clark, Jr D.L., et al., "Detection of *Mycobacterium avium* subspecies paratuberculosis: Comparing fecal culture versus serum enzyme-linked immunosorbent assay and direct fecal polymerase chain reaction." J. Dairy Sci., 2008, 91:2620-2627.
Yokomizo, Y., et al., "A method for avoiding false-positive reactions in an enzyme-linked immunosorbent assay (ELISA) for the diagnosis of bovine paratuberculosis." Jpn. J. Vet. Sci., 1985, 47:111-119.
Samanich, K.M., et al., "Serodiagnostic potential of culture filtrate antigens of *Mycobacterium* tuberculosis." Clin. Diagn. Lab. Immunol., 2000, 7:662-668.
Waters, W.R., et al., "Early antibody responses to experimental *Mycobacterium* bovis infection of cattle." Clin. Vaccine. Immunol., 2006, 13:648-654.
Cho, D., and Collins, M.T., "Comparison of the proteosomes and antigenicities of secreted and cellular proteins produced by *Mycobacterium* paratuberculosis." Clin. Vaccine. Immunol., 2006, 13:1155-1161.
Shin, S.J., et al., "Diagnosis of bovine paratuberculosis by a novel enzyme-linked immunosorbent assay based on early secreted antigens of *Mycobacterium avium* subsp. paratuberculosis." Clin. Vaccine. Immunol., 2008, 15:1277-1281.

(Continued)

*Primary Examiner* — Rodney P Swartz
(74) *Attorney, Agent, or Firm* — Bereskin & Parr LLP/ S.E.N.C.R.L., s.r.l.; Laurence MacPhie

(57) ABSTRACT

Described are methods and products useful for identifying subjects with *Mycobacterium avium* subspecies *paratuberculosis* (MAP). A number of protein antigens secreted into culture filtrate by MAP are identified and binding proteins selective for these antigens are demonstrated to be useful for detecting subjects with MAP infections including subjects with Johne's disease.

20 Claims, 16 Drawing Sheets

(56) References Cited

OTHER PUBLICATIONS

Bannantine, J.P., et al., "Early antibody response against *Mycobacterium avium* subspecies paratuberculosis antigens in subclinical cattle." Proteome Sci., 2008, 6:5, doi: 10.1186/1477-5956-6-5.

Merkal, R. and Curran, B., "Growth and metabolic characteristics of *Mycobacterium* paratuberculosis." Appl. Microbiol., 1974, 28:276-279.

Blum, H., et al., "Improved silver staining of plant proteins, RNA and DNA in polyacrylamide gels." Electrophoresis., 1987, 8:93-99.

Woodward, M.P., et al., "Detection of monoclonal antibodies specific for carbohydrate epitopes using periodate oxidation." J. Immunol. Methods., 1985, 78:143-153.

Nadkarni, V., and Linhardt, R., "Enhancement of diaminobenzidine colorimetric signal in immunoblotting." BioTechniques, 1997, 23:385-388.

Mattow, J., et al., "Comparative proteome analysis of culture supernatant proteins from virulent *Mycobacterium* tuberculosis H37Rv and attenuated M. bovis BCG Copenhagen." Electrophoresis, 2003, 24:3405-3420.

Santema, W., et al., "Searching for proteins of *Mycobacterium avium* subspecies paratuberculosis with diagnostic potential by comparative qualitative proteomic analysis of mycobacterial tuberculins." Vet. Microbiol., 2009, 138:191-196.

Cho, D., et al., "Identification of proteins of potential diagnostic value for bovine paratuberculosis." Proteomics, 2006, 6:5785-5794.

Leroy, B., et al., "Antigen discovery: a postgenomic approach to paratuberculosis diagnosis." Proteomics, 2007, 7:1164-1176.

He, Z., and De Buck, J., "Localization of proteins in the cell wall of *Mycobacterium avium* subsp. paratuberculosis K10 by proteomic analysis." Proteome Sci., 2010, 8:21. doi: 10.1186/1477-5956-8-21.

Gomez, M., et al., "Identification of Secreted Proteins of *Mycobacterium* tuberculosis by a Bioinformatic Approach." Infect. Immun., 2000, 68:2323-2327.

Malen, H., et al., "Comprehensive analysis of exported proteins from *Mycobacterium* tuberculosis H37Rv." Proteomics, 2007, 7:1702-1718.

Digiuseppe Champion, P.A., and Cox, J.S., "Protein secretion systems in Mycobacteria." Cell. Microbiol., 2007, 9:1376-1384.

Daleke, M.H., et al., "General secretion signal for the mycobacterial type VII secretion pathway." Proc. Natl. Acad. Sci. USA., 2012,109:11342-11347.

Jeffery, C.J., "Moonlighting proteins." Trends. Biochem. Sci., 3327-Pos, Board B55, 1999, 24:8-11.

Henderson, B., and Martin, A., "Bacterial virulence in the moonlight: multitasking bacterial moonlighting proteins are virulence determinants in infectious disease." Infect. Immun., 2011, 79:3476-3491.

Tunio, S.A., et al., "The moonlighting protein fructose-1, 6-bisphosphate aldolase of Neisseria meningitidis: surface localization and role in host cell adhesion." Mol. Microbiol., 2010, 76:605-615.

Cehovin, A., et al., "Comparison of the moonlighting actions of the two highly homologous chaperonin 60 proteins of Mycobacterium tuberculosis." Infect. Immun., 2010, 78:3196-3206.

Raghavan, S., et al., "Secreted transcription factor controls Mycobacterium tuberculosis virulence." Nature, 2008, 454:717-721.

Radosevich, T.J., et al., "Proteome and differential expression analysis of membrane and cytosolic proteins from *Mycobacterium avium* subsp. paratuberculosis strains K-10 and 187." J. Bacteriol., 2007, 189:1109-1117.

Weigoldt, M., et al., "Differential proteome analysis of *Mycobacterium avium* subsp. paratuberculosis grown in vitro and isolated from cases of clinical Johne's disease." Microbiology, 2011, 157:557-565.

Weigoldt, M., et al., "Metabolic adaptation of *Mycobacterium avium* subsp. paratuberculosis to the gut environment." Microbiology, 2013, 159:380-391.

Xolalpa, W., et al., "Identification of novel bacterial plasminogen-binding proteins in the human pathogen *Mycobacterium* tuberculosis." Proteomics, 2007, 7:3332-3341.

Paustian, M.L, et al., "Comparative genomic hybridizations reveal genetic regions within the *Mycobacterium avium* complex that are divergent from *Mycobacterium avium* subsp. paratuberculosis isolates." J. Bacteriol., 2005, 187:2406-2415.

NCBI GeneBank Accession No. NP_962568.1 (2013), "hypothetical protein MAP3634 [*Mycobacterium avium* subsp. paratuberculosis K-10]", [Retrieved form the Internet on Oct. 21, 2014 (Oct. 21, 2014) <http://www.ncbi.nlm.nih.gov/protein/NP_962568>.

NCBI GeneBank Accession No. YP_007973175.1 (2013), "putative conserved membrane protein [*Mycobacterium avium* subsp. paratuberculosis Map4]", [Retreived from the Internet on Oct. 21, 2014 (Oct. 21, 2014), <http://www.ncbi.nlm.nih.gov/protein/YP_007973175.1>.

NCBI GeneBank Accession No. NP_962362.1 (2013), "hypothetical protein MAP3428c [*Mycobacterium avium* subsp. paratuberculosis K-10]", Retrieved from the Internet on Oct. 21, 2014) (Oct. 21, 2014), <http://www.ncbi.nlm.nih.gov/protein/NP_962362>.

Facciuolo, A. et al., "Novel secreted antigens of Mycobacterium paratuberculosis as serodiagnostic biomarkers for Johne's disease in cattle." Clinical and Vaccine Immunology, Dec. 2013, vol. 20, No. 12, pp. 1783-1791, (published Online Oct. 2013).

Cossu, A., et al., "Gene expression profiling of Mycobacterium avium subsp. paratuberculosis in simulated multi-stress conditions and within THP-1 cells reveals a new kind of interactive intramacrophage behaviour." BMC Microbiology, 2012, vol. 12:87.

International Search Report completed Nov. 4, 2014 and Written Opinion completed Nov. 14, 2014 for corresponding PCT Application No. PCT/CA2014/050914.

Poster Presentation titled, "Identifying immunogenic proteins of *Mycobacterium avium* subspecies paratuberculosis for potential diagnostic markers" presented at University of Guelph (Graduate Student Symposium), Guelph, ON, Canada, Apr. 26, 2011.

Poster Presentation titled, "Using Proteomic Tools to Identify Diagnostic Biomarkers for Johne's Disease", presented at Jniversity of Guelph (Graduate Student Symposium), Guelph, ON, Canada, Apr. 30, 2012.

\* cited by examiner

MAP0196c (SEQ ID NO 1)

MSQAPEKDLPEAGEAPAVETTAASAFLWPRSLQARATRRALLLTALGGLLIAGLVTALPV
GGTGSGRLLDASPVRSTGAKSDAAFNRAASGECLMWPDTTPESAKIVNCGDDHKFEVAES
IDMRTFPGSEYGPNAAPPTPARIQQITQEQCEAAVRNYLGPKFDPNSKFTVSLLWPGDRA
WRQGGDRRMLCGLQLPGANNQQQVFKGKVADVDQSKIWPAGTCLGIDSATNQPTDVPVDC
AAPHAMEVTGTVNLAEKFPGALPAEPDQDAFIKDSCTKMTDAYLAPVKLRTTTLTLIYPT
VPLASWTAGSREVACSIGATLGNGGWATLLNSAKGQLLINGQPPVPPPDIPEERLSMPPI
PLQAPAQSPSTQSGSAAAPEMPRNNQHLPGQQPVVTQPPQAPPPPVDNGAPPPANPAPEA
PPAPVPPPAAPPPPPPPAPEAPPGGPPPAG

MAP0471 (SEQ ID NO: 2)

MTWAYAANVLDLEPRGPLPTEIYWRRGLAVGIAVVVIGVVAAAVIAFMGHSAGAKPANA
DKPNSAQSKPGSPAPQAPAPPGPEGPAPAVPPAQGQNPETPTPTAAVQPPPVLKEGDDCP
DSTLAVKGLTNAPQYFIGDQPKFTMVVTNIGLVACKRDVGAAVLAAYVYSLDNKRLWSNL
DCAPSNETLIKTFTPGEQVTTAVTWTGMGSAPHCPLPRPAIGPGTYNLVVQLGNLRSQPV
PFIMNQPPPPPGPVPGPGQPGAVPQPEAPPVPPPPAG

MAP1981c (SEQ ID NO: 3)

MKADVAQQRSLLELANVDAELSRLAHRAEHLPEQQACERMQQEYDAAGDRLGAVRIALED
IDAHVLRLEAEVDAVRQREDRDRSLLQSGAIDAKQLADLQHELETLQRRQTSLEDSLLEV
MERREELQAQLDGEQQALKELEAEMATARRDLDAARGEISESRALHSSRRDALSAELDPE
LFALYERQRARGGPGAGQLLGRRCGACRLEIDRGELSRISAAAEDDVVRCPECGAILLRV
KGSGQ

MAP1569 (SEQ ID NO: 4)

MDQVEATSTRRKGLWTTLAITTVSGASAVAIALPATSHADPEVPTVPPSTATAPPAAPA
PNGQPAPNAQPAPGAPAPNGQPAPAAPAPNDPNAAPPPVGAPPNGAPPPPVDPNAPPPPP
ADPNAGRIPNAVGGFSYVLPAGWVESDASHLDYGSALLSKVTGPPPMPDQPPPVANDTRI
VMGRLDQKLYASAEANNAKAAVRLGSDMGEFFMPYPGTRINQDSTPLNGANGSTGSASYY
EVKFSDASKPNGQIWTGVIGSANGGNAQRWFVVWLGTSNDPVDKVAAKALAESIQAWTPP
AAPPAAPGGPGAPAPGAPGTPAAPGAPAAPAPAAPGAPAAPGAPAPGQAPAVEVSPTPTP
TPQQTLSA

MAP0281 (SEQ ID NO: 5)

MTRKAEIVAVFAICTAFMTASGAFGGFAARADDPEILYNGINQLRQACGPIAEDPRLTEA
AQQHADDMLRNGVSGHIGSDGSSPQARIAAAGYRSRYSGEIVFWATGSAATPSEALDMWM
QSPPHRAIILNCGFNAGGFATARDGNKMTAVGDFATS

FIG. 5

MAP1718c (SEQ ID NO: 6)

MAFSHIASKTTAATAALAAAGLLAAAPAFADPQVLQFGQMAEISSNGGTIDYTVSNLQPS
GHNDGVWYSDVTAKGVSGNAVPNIADFNARAVNSSTFAVMKGNQTDGLPEGPLPLGTPVT
GRLYFDVRNGTNPDSVVYRDAGGTDKVVWKS

MAP3428c (SEQ ID NO: 7)

MSGGCARIWRMNLRGWPVVGPAIGTVVAVALSVVAITCGPAPRAAADGCPDVQLIFARGT
AEPPGLGAVGDALFAALQPALGNRNVDAYAVNYPASYNFLTTADGANDARDHIAEMVDRC
PSTRLVLGGFSQGAAAVSMLAGVPPVGQRIGNFGSAPPLDPGLASKIAAVAVFGNPGNRF
NTPLSTTGAFAGRAIDLCSDGDPVCVVGGRDRDAHHVYEDPPYPAQAAGFIAGRV

MAP3634 (SEQ ID NO: 8)

MSGGMPMSGWTRGTLFAALNAAVVSVVGLALVLSAGPALADPDPAPADPGAVAAPPGPPA
PPDPLAPPPPPDPLAPPPPAAPPAPWLPPAAQPAAAPAAGQDPTPFTGTPPFGPPTFVPK
TGSTVGVAQPIIINFPGRVDDAGAAISAVHVSSVPPVPGKFYWMTPTQLRWRPLSFWPAH
TAVTVDAGGTVTNFQTGDTLVATADDATHQLTVTRNGTVEKTFPMSMGMTAGNHQTPNGT
YYVQDKKASVVMDSSTYGVPVNSTYGYKVTVEDAVRFDNVGDYVHSAPWSVDDQGKRDVS
HGCINISPANAKWFFDNFGPGDPIIVKNSSGGDYKKNDGSADWMN

MAP2785c (SEQ ID NO: 9)

MHPAGNCRKRCESFAVRRRRQFPRQALPRAGARRDADRRRVWDNRCAMRLFLGLCALAAT
IGLAAPAHADIDNDQDFLKDLRDAGITYQDAGNAITIGKSVCELLDDGQSDAKIVTDLRN
QNPAFQGASAAKFTYLSAAHYCPKYITGEDRGPKPEGAVGN

MAP2786c (SEQ ID NO: 10)

MKLFLIVAGFAAVIGLAVPARADSTDDAFVASLDKAGIKYGDADKAAGAGKWVCTTLQGG
KQMSDVVSTLQSKNSNLSDDHANTFAAIAVNAYCPDQASSITPATPTDTPPSTS

MAP1693c (SEQ ID NO: 11)
MTAVNSVRTFSAAAFAACFTAAAAMLAGAGTAGAADSCPTAAPPSGGTPDWTLTGTTGSV
AVTGSTDTAAPVVNVTAPFSVTQTQVHTLRAGDGPAVPGTARVSVCYMGVNGRDGTVFDS
SYQRGAPVDFPLGGVVPGFQKAIAGQKVGSTVAVAMTSADGYPDGQPSAGIRPGDTLVFA
IKILGATT

FIG. 5 (CONT.)

A
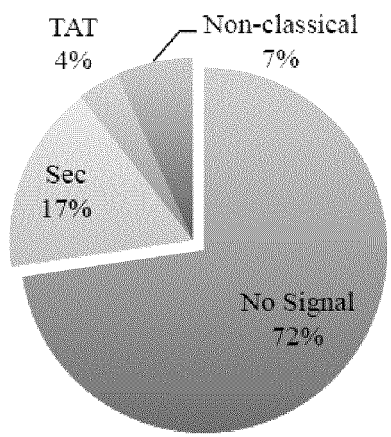
B
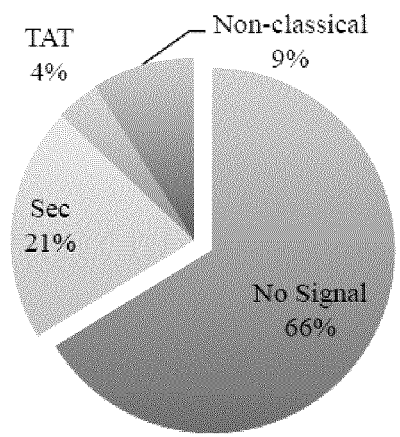
FIG. 6

US 9,879,057 B2

BIOMARKERS FOR *MYCOBACTERIUM AVIUM PARATUBERCULOSIS* (MAP)

CROSS REFERENCE TO RELATED APPLICATIONS

This application is a national phase entry of PCT/CA2014/050914 filed Sep. 24, 2014 (which designates the U.S.) which claims the benefit of U.S. Provisional Application No. 61/881,756, filed Sep. 24, 2013, titled "BIOMARKERS FOR *MYCOBACTERIUM AVIUM PARATUBERCULOSIS* (MAP),", which is herein incorporated by reference in its entirety.

INCORPORATION OF SEQUENCE LISTING

A computer readable form of the Sequence Listing "6580-P44673US01 SequenceListing.txt" (24,576 bytes), submitted via EFS-WEB and created on Mar. 16, 2016, is herein incorporated by reference.

FIELD OF THE DISCLOSURE

The present disclosure relates to biomarkers for *Mycobacterium avium* subspecies *paratuberculosis* (MAP) and more specifically to protein biomarkers for the detection of MAP and associated methods.

BACKGROUND OF THE DISCLOSURE

Johne's disease is a chronic gastroenteritis affecting ruminant animals worldwide with national prevalence rates of 32% in Canada, and 68% in the U.S. (1, 2). Calves are most susceptible and once colonized they remain asymptomatic for 2 to 5 years while shedding *M. avium* subsp. *paratuberculosis* (MAP) in feces, colostrum, and milk (3). As there is no effective or approved treatment for Johne's disease, control of MAP at the herd-level requires identification of infected animals, specifically MAP-shedders, and their removal from the herd (4). In addition, certain calf rearing, cleaning, and animal husbandry practices have shown promise of reducing MAP prevalence (5). To accurately detect MAP-infected animals a number of methodologies have been employed including serodiagnosis by ELISA, detection by PCR amplification of MAP-specific sequences in feces and milk, measurement of interferon-gamma secretion by T-cells, and bacterial culture of fecal and milk samples. However, variables such as antigen-specificity and sensitivity, reproducibility, time to colony detection, PCR inhibitors in feces and milk, and cross-reactivity are all factors that currently limit the efficacy of these methods (6). Serodiagnosis by ELISA has been recommended as the primary methodology as this platform is relatively less laborious, rapid, cost-effective, and the results are simple to interpret (7).

Commercially available ELISAs for Johne's disease have high specificity (90-99%), but all suffer from low sensitivity (13.5% to 42%) (8). The antigen compositions of these ELISAs are mostly proprietary in nature, but have been shown to contain a mixture of cellular proteins and/or purified protein derivative (9). The sensitivity of these assays was reported to be lowest (5-7%) in cattle shedding low levels of MAP, and only reached sensitivity values of 70-80% when high levels of MAP are detected in feces (10). Moreover, preabsorption of serum with *Mycobacterium phlei* crude protein lysates has improved the specificity of commercial ELISAs by removing cross-reactive antibodies (11).

The sensitivity of serodiagnostics improved with the use of MAP culture filtrate (CF) proteins, and similarly for other *mycobacterial* pathogens including *M. bovis* and *M. tuberculosis* (6, 12, 13). Compared to cellular proteins, MAP CF proteins showed greater reactivity with serum from MAP-infected cattle both with respect to the number of antigens detected and in the intensity of reaction on immunoblots (14). The use of MAP CF antigens in ELISAs increased assay sensitivity by 25% over commercial ELISAs in low MAP-shedding cattle (15). However, antigen selection remains a challenge, as there is no single MAP-specific antigen that is recognized by all infected cattle, especially those in early and subclinical stages of disease. Recently, early serodiagnosis was addressed using experimentally infected calves, and screening for antibody responses to a panel of 96 recombinant MAP-antigens (16). Antibody responses were detected as early as 70 days post-infection; however, fluctuations in antibody response and epitope specificity were observed over 321 days (16). These data suggest the need for a standardized cocktail of antigens for incorporation into a single ELISA for detection at all stages of disease in infected cattle.

There remains a need for new and improved biomarkers for MAP as well as new and improved methods for identifying animals with MAP infections and/or Johne's disease.

SUMMARY OF THE DISCLOSURE

In one aspect, the inventors have identified a number of MAP-specific, immunodominant antigens within the MAP culture filtrate (CF) proteome. As set out in Example 1, 162 unique MAP secreted proteins listed in Table 2 were captured and resolved using a 2-step fractionation method and reversed-phase liquid chromatography. 66 proteins of these proteins do not appear to have been previously described as secreted in MAP CF. Four protein antigens MAP0196c (SEQ ID NO: 1), MAP0471 (SEQ ID NO: 2), MAP1981c (SEQ ID NO: 3), and MAP1569 (SEQ ID NO: 4) were identified that reacted with 35 serum samples from MAP-infected cows ranging from low to high shedders. Remarkably, no evidence of cross-reactivity was seen with negative control sera obtained from fecal-culture and ELISA negative cows from a Johne's Disease-free herd, or in 2-month-old calves. Furthermore, the inventors have identified an additional subset of the 66 proteins that are expected to be particularly useful as biomarkers for MAP based on their reactivity with sera from cows that are infected with MAP (fecal-culture and ELISA positive cows), including MAP0196c (SEQ ID NO: 1), MAP0471 (SEQ ID NO: 2), MAP1981c (SEQ ID NO: 3), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9) and MAP2786c (SEQ ID NO: 10).

As set out in Example 2, the inventors recombinantly expressed a number of MAP protein including MAP0196c (SEQ ID NO: 1), MAP0471 (SEQ ID NO: 2), MAP1981c (SEQ ID NO: 3), MAP1569 (SEQ ID NO: 4), MAP3634 (SEQ ID NO: 8) and MAP1693c (SEQ ID NO: 11). Rats were then immunized with the MAP recombinant proteins and the specificity of the resulting antibodies was determined. As set out in Examples 3 and 4, the rat polyclonal antibodies detected native MAP secreted proteins with minimal cross-reactivity to other MAP proteins and appeared specific to MAP protein epitopes. In addition, antibodies to four of the MAP recombinant proteins MAP0471 (SEQ ID NO: 2), MAP1569 (SEQ ID NO: 4), MAP3634 (SEQ ID NO: 8) and MAP1693c (SEQ ID NO: 11) were detected in sera from MAP fecal-culture positive cows, but absent in serum from MAP-negative calves (Example 5).

Accordingly, in one aspect of the disclosure there Is provided a MAP protein listed in Table 2. In one embodiment, the protein is secreted in MAP culture filtrate. In one embodiment, the protein is selected from MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) and MAP1693c (SEQ ID NO: 11). In one embodiment, the protein is selected from MAP0196c (SEQ ID NO: 1), MAP0471 (SEQ ID NO: 2), MAP1981c (SEQ ID NO: 3), MAP1569 (SEQ ID NO: 4), MAP3634 (SEQ ID NO: 8) and MAP1693c (SEQ ID NO: 11). In a preferred embodiment, the protein is selected from MAP0471 (SEQ ID NO: 2), MAP3634 (SEQ ID NO: 8) and MAP1693c (SEQ ID NO: 11). In one embodiment, the protein is an antigen. For example, in one embodiment, the protein binds to sera from an animal infected with MAP. In one embodiment, the protein exhibits increased binding to sera from an animal infected with MAP relative to a sera from an uninfected animal. In one embodiment, the protein exhibits increased binding to sera from an animal infected with MAP relative to sera from an animal exposed to *Mycobacterium avium* subspecies *hominissuis* (MAH) or other species of *Mycobacterium*.

Also provided are nucleic acid molecules encoding for a MAP protein listed in Table 2. In one embodiment, the nucleic acid molecule encodes for a protein selected from MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) and MAP1693c (SEQ ID NO: 11). In one embodiment, the nucleic acid molecule encodes for a protein selected from MAP0196c (SEQ ID NO: 1), MAP0471 (SEQ ID NO: 2), MAP1981c (SEQ ID NO: 3), MAP1569 (SEQ ID NO: 4), MAP3634 (SEQ ID NO: 8) and MAP1693c (SEQ ID NO: 11). In a preferred embodiment, the protein is selected from MAP0471 (SEQ ID NO: 2), MAP3634 (SEQ ID NO: 8) and MAP1693c (SEQ ID NO: 11). Also provided is a recombinant expression vector comprising a nucleic acid molecule encoding for a MAP protein as described herein. Also provided is a host cell transfected with a recombinant expression vector comprising a nucleic acid molecule encoding for a MAP protein as described herein.

In one embodiment, there is provided a method for the production of a MAP protein comprising culturing a host cell transfected with a vector comprising a nucleic acid molecule encoding for the MAP protein as described herein. In one embodiment, the nucleic acid molecule is codon optimized for expression in a particular host cell, such as *E. coli*. In one embodiment, the MAP protein is selected from MAP0196c (SEQ ID NO: 1), MAP0471 (SEQ ID NO: 2), MAP1981c (SEQ ID NO: 3), MAP1569 (SEQ ID NO: 4), MAP3634 (SEQ ID NO: 8) and MAP1693c (SEQ ID NO: 11). In a preferred embodiment, the protein is selected from MAP0471 (SEQ ID NO: 2), MAP3634 (SEQ ID NO: 8) and MAP1693c (SEQ ID NO: 11). Optionally, the method further comprises isolating the recombinant MAP protein from the culture filtrate or supernatant.

In one embodiment, there is provided a method for the production of a MAP protein antibody comprising immunizing a mammal with a MAP protein selected from Table 2 or an immunogenic composition as described herein to elicit an antibody response in the mammal. In one embodiment, the method comprises immunizing a mammal with a protein selected from MAP0196c (SEQ ID NO: 1), MAP0471 (SEQ ID NO: 2), MAP1981c (SEQ ID NO: 3), MAP1569 (SEQ ID NO: 4), MAP3634 (SEQ ID NO: 8) and MAP1693c (SEQ ID NO: 11). In a preferred embodiment, the protein is selected from MAP0471 (SEQ ID NO: 2), MAP3634 (SEQ ID NO: 8) and MAP1693c (SEQ ID NO: 11). In one embodiment, following immunization, antisera is obtained from the mammal and polyclonal antibodies to the MAP protein are isolated from the sera. In one embodiment, the method comprises isolating antibody-producing cells from the mammal, producing hybridoma cells from the antibody-producing cells and optionally isolating monoclonal antibodies to the MAP protein from the hybridoma cells.

In another aspect of the disclosure, there is provided an immunogenic composition comprising one or more of the proteins described herein such as a protein listed in Table 2. For example, in one embodiment, the immunogenic composition comprises one, two, or three or greater than three proteins selected from MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) and MAP1693c (SEQ ID NO: 11). In one embodiment, the immunogenic composition comprises one, two or three proteins selected from MAP0196c (SEQ ID NO: 1), MAP0471 (SEQ ID NO: 2) and MAP1981c (SEQ ID NO: 3). In another embodiment, the immunogenic composition comprises one, two or three proteins selected from MAP0471 (SEQ ID NO: 2), MAP3634 (SEQ ID NO: 8) and MAP1693c (SEQ ID NO: 11). In one embodiment, the immunogenic composition comprises MAP3634 (SEQ ID NO: 8). Optionally, the immunogenic composition also includes a pharmaceutically acceptable excipient, carrier, buffer, stabilizer, or mixtures thereof. In some embodiments, the immunogenic composition also comprises an immunostimulatory component, such as an adjuvant. In some embodiments, the immunogenic compositions described herein are useful for preparing binding proteins such as antibodies for detecting the presence of MAP.

In one aspect of the disclosure, there is provided a binding protein that selectively binds to a protein described herein, such as a protein listed in Table 2. In one embodiment, the binding protein is an antibody, such as a polyclonal antibody, monoclonal antibody or fragment thereof. In one embodiment, the binding protein is conjugated to a detectable label. In one embodiment, the detectable label is a fluorescent compound, chemiluminescent compound or an enzyme. In one embodiment, the detectable label is suitable for use in an Enzyme-Linked immunoabsorbent assay (ELISA). In one embodiment, the binding protein is useful for the detecting MAP in a sample from a subject.

In one embodiment, the binding protein is an antibody that selectively binds to a protein selected from MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) and MAP1693c (SEQ ID NO: 11). In one embodiment, the binding protein is an antibody that selectively binds to a protein selected from MAP0471 (SEQ ID NO: 2), MAP3634 (SEQ ID NO: 8) and MAP1693c (SEQ ID NO: 11). In one embodiment, the binding protein is an antibody that selectively binds to MAP3634 (SEQ ID NO: 8).

In another aspect of the disclosure, there is provided a kit comprising one or more of the binding proteins as described herein. Optionally, the kit further comprises a container suitable for storing one or more binding proteins as described herein, medium suitable for formation of an antigen-antibody complex, reagents for detection of the antigen-antibody complexes and/or instructions for the use thereof. In one embodiment, the kit is useful for detecting the presence of MAP in a sample from a subject. Also provided is the use of the binding proteins and/or kits as described herein for detecting MAP in a sample from a subject.

In one aspect of the disclosure, there is provided a method of identifying *Mycobacterium avium* subspecies *paratuberculosis* (MAP) in a sample from a subject. In another aspect of the disclosure, there is provided a method of identifying *Mycobacterium avium* subspecies *paratuberculosis* (MAP) in a sample in vitro. In one embodiment, the method comprises determining the presence or absence of one or more proteins selected from Table 2 in a sample from the subject. In one embodiment, the presence of one or more of the proteins listed in Table 2 in the sample indicates the presence of MAP in the sample or in the subject.

MAP is the causative agent for Johne's disease in cattle. Accordingly, in one embodiment, the subject has or is suspected of having Johne's disease. Optionally, in some embodiments the subject is pre-symptomatic for Johne's disease. In one embodiment, the method comprises testing a plurality of subjects for MAP as described herein and removing or quarantining those subjects identified as having MAP from those subjects not identified as having MAP. In one embodiment, the plurality of subjects is a herd of animals, such as a herd of cattle or a herd of other ruminants.

In one embodiment, the method comprises determining the presence or absence of at least one protein selected from MAP0196c (SEQ ID NO: 1), MAP0471 (SEQ ID NO: 2), MAP1981c (SEQ ID NO: 3), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9) MAP2786c (SEQ ID NO: 10) and MAP1693c (SEQ ID NO: 11). In one embodiment, the method comprises determining the presence or absence of at least one protein selected from MAP0196c (SEQ ID NO: 1), MAP0471 (SEQ ID NO: 2) and MAP1981c (SEQ ID NO: 3). In one embodiment, the method comprises determining the presence or absence of at least one protein selected from MAP0471 (SEQ ID NO: 2), MAP3634 (SEQ ID NO: 8) and MAP1693c (SEQ ID NO: 11). In one embodiment, the method comprises determining the presence of absence of MAP3634 (SEQ ID NO: 8). Optionally, the methods described herein also include determining the presence or absence of MAP1569 (SEQ ID NO: 4).

In one embodiment, the sample comprises any biological material, fluid or tissue from the subject that can be assayed for one or more of the proteins listed in Table 2. For example, in one embodiment, the sample comprises blood, feces, milk or colostrum. Optionally, the methods described herein also include obtaining or providing a sample from a subject. In one embodiment, the subject is a ruminant, such as a cow.

In one embodiment, the methods described herein include detecting the presence or absence of one or more proteins in a sample from a subject, such as a protein listed in Table 2. In one embodiment, detecting the presence or absence of one or more proteins comprises contacting the sample with one or more binding proteins that are selective for the proteins listed in Table 2 as described herein. For example, in one embodiment the one or more proteins are detected in an Enzyme-Linked Immunosorbent Assay (ELISA). In some embodiment, the one or more proteins are detected using other methods or assays known in the art to detect proteins such as mass spectroscopy.

In one embodiment, the methods described herein include determining a level of the one or more proteins in the sample and comparing the level of the one or more proteins in the sample with a control. In one embodiment, the magnitude of the level of the one or more proteins is indicative of severity of MAP infection in the subject.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

One or more embodiments of the disclosure will now be described in relation to the drawings in which:

FIG. 5 shows the amino acid sequence of protein antigens identified as being particularly useful for the detection of MAP including MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) and MAP1693c (SEQ ID NO: 11).

FIG. 6 shows bioinformatic analysis for secretory signal peptides of MAP CF proteins. SignalP 2.0, PRED-TAT, and SecretomeP 2.0 were used to predict the presence of canonical secretory peptides among all proteins identified in this study (A), or the novel proteins only (B).

DETAILED DESCRIPTION

I. Definitions

Figure 1:
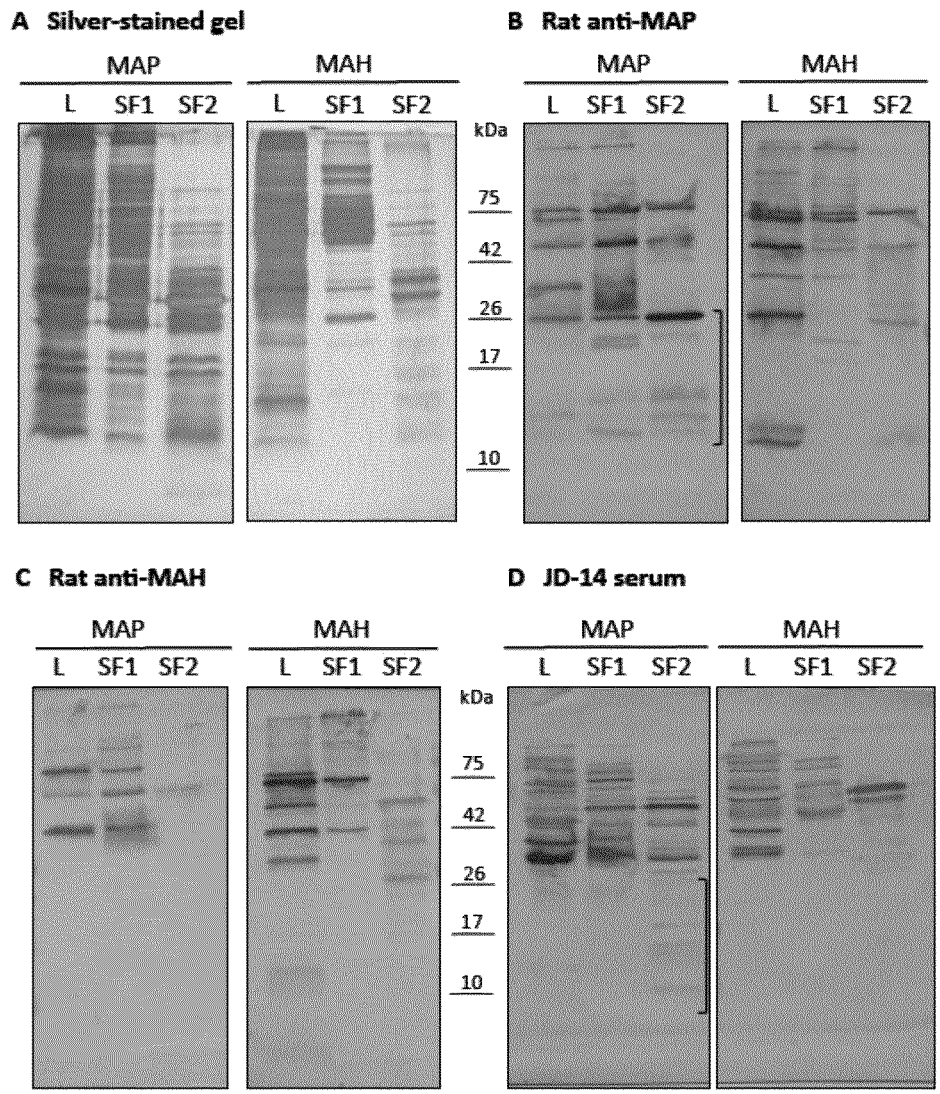
FIG. 1 shows comparative 1D SDS-PAGE, and immunoblots of MAP and MAH whole-cell lysates (L), SF1, and SF2 preparations. (A) Silver-stained 12% w/v polyacrylamide gel. Immunoblots showing reaction with polyclonal rat anti-MAP sera (B), polyclonal rat anti-MAH sera (C), and JD-14 serum (D). Each sample lane contained 20 µg of protein. The blots were subjected to periodate oxidation immediately after electrotransfer and before incubation with blocker and serum. The open bracket in (B) and (D), lane MAP SF2 denotes the <26 kDa proteins detected in MAP but not MAH CF. Molecular weight standards are listed.

The term "subject" as used herein includes all members of the animal kingdom including mammals, and suitably refers to any animals susceptible to infection with *Mycobacterium avium* subspecies *paratuberculosis* (MAP). In one embodiment, the "subject" is a ruminant. Optionally, the term "subject" includes cows that have Johne's disease or are suspected of having Johne's disease. In one embodiment, the subject is an animal with a MAP infection who is asymptomatic.

The term "identifying" as used herein refers to a process of determining a subject's likelihood of having a *Mycobaterium avium* subspecies *paratuberculosis* (MAP) infection. As used herein, identifying a subject at risk of having a *Mycobaterium avium* subspecies *paratuberculosis* (MAP) infection includes identifying a subject at risk of progressing to a more severe form of the disease state or infection, such as Johne's disease. Accordingly, the invention can be used to detect or monitor the appearance and progression of MAP infection and/or Johne's disease in a subject or group of subjects. In one embodiment, the methods are used to provide a prognosis for a subject with Johne's disease or suspected of having Johne's disease. Optionally, the term "identifying" includes methods of screening for and identifying subjects with a MAP infection from a population of subjects.

As used herein, "Johne's disease" refers to a chronic, gastroenteritis of cattle caused by infection with *Mycobaterium avium* subspecies *paratuberculosis* (MAP). Symptoms of Johne's disease include, but are not limited to, weight loss, diarrhea, decreased milk production, intermandibular edema, and cachexia.

The term "sample" refers to any fluid or other specimen from a subject which can be assayed for one or more of the proteins listed in Table 2. In some embodiment, the sample is a blood sample such as whole blood, serum or plasma. In one embodiment, the sample is a fecal sample. In one embodiment, the sample is a urine sample. In one embodiment, the sample is a colostrum sample or milk sample. In one embodiment, the sample is a tissue sample. In one embodiment, the sample is a semen sample. In one embodiment, the sample is from a subject with a MAP infection or suspected of having a MAP infection. In one embodiment, the sample may be a sample from a cell culture. Optionally, the sample is treated to remove cell debris or other contaminants that may interfere with detecting one or more proteins listed in Table 2 in the sample.

As used herein, the term "binding protein" refers to an agent that selectively binds to a protein listed in Table 2 that can be used to directly or indirectly detect the protein. Examples of binding proteins include, but are not limited to, antibodies, antibody mimics and the like.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and bispecific antibody fragments.

Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

II. Proteins, Compositions and Antibodies

In one aspect of the disclosure, the inventors have identified proteins that are secreted into culture filtrate by MAP, including the proteins listed in Table 2. In one embodiment, these proteins are useful as biomarkers for the detection of MAP in a sample from a subject. In one embodiment, these proteins are useful as antigens.

In one embodiment there is provided an isolated protein listed in Table 2. In one embodiment, there is also provided a protein with sequence identity to a protein listed in Table 2, wherein the protein is secreted into culture filtrate by MAP and/or is an antigen. In one embodiment, the protein is MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) or MAP1693c (SEQ ID NO: 11). Also provided are proteins comprising, consisting essentially of, of consisting of at least 80%, 85%, 90%, 95%, 96%, 97%, 98% or 99% sequence identity to MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9) or MAP2786c (SEQ ID NO: 10), or MAP1693c (SEQ ID NO: 11). In one embodiment, there is provided an epitope within a protein selected from MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) or MAP1693c (SEQ ID NO: 11).

In one embodiment, there are provided immunogenic compositions comprising one or more of the proteins described herein such as a protein listed in Table 2. In one embodiment, the immunogenic composition comprises two or more, three or more, four or more or more than 5 proteins selected from MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5), MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) and MAP1693c (SEQ ID NO: 11). In one embodiment, the immunogenic compositions are useful for the production of antibodies. In one embodiment, the immunogenic composition comprises one or more, two or more or three proteins selected from MAP3634 (SEQ ID NO: 8), MAP0471 (SEQ ID NO: 2) and MAP1693c (SEQ ID NO: 11).

In another aspect of the disclosure, there is also provided binding proteins such as antibodies that selectively bind a protein listed in Table 2. Also provided are immunoconjugates comprising a binding protein described herein conjugated to another molecule, such as a detectable label.

Antibodies that selectively bind a protein antigen may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody-producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with the peptide and the monoclonal antibodies can be isolated.

In one embodiment of the invention, the binding proteins, such as antibodies or antibody fragments, that bind to a protein listed in Table 2 are labeled with a detectable marker. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$ or $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

Also provided are compositions and kits that include one or more of the binding proteins described herein. For example, in one embodiment, the invention relates to a composition comprising one or more antibodies selective for a protein listed in Table 2, optionally provided together in a container. In one embodiment, there is provided a kit comprising one or more antibodies selective for a protein listed in Table 2, with instructions for use of the kit for identifying MAP in a sample from a subject. In one embodiment, there is also provided compositions and kits comprising a plurality of binding proteins as described herein that are suitable for detecting a plurality of proteins listed in Table 2 using multiplex technology. The application also provides kits and compositions comprising the binding proteins disclosed herein, preferably antibodies and antibody fragments, with a pharmaceutically acceptable excipient, carrier, buffer or stabilizer. In one embodiment, the kits are useful for performing a method as described herein for identifying MAP in a subject with a binding protein such as an antibody.

III. Methods and Uses

In one aspect of the disclosure, there is provided a method for identifying a subject with a MAP infection. In one embodiment, the method comprises determining the presence or absence of one or more of the protein biomarkers listed in Table 2 in a sample from the subject. As set out in Example 1, these proteins have been identified in MAP culture filtrate and are therefore expected to be indicative of MAP infection in a subject with a MAP infection, such as a subject with Johne's disease. Furthermore, as set out in Example 5, the recombinant proteins MAP1569, MAP0471, MAP3634, and MAP1693c were detected using sera from MAP fecal-culture positive cows but not using sera from MAP-negative calves.

In one embodiment, the presence of one or more proteins selected from MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5) MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) and MAP1693c (SEQ ID NO: 11) in a sample from a subject is indicative of a MAP infection in the subject. In one embodiment, the presence of one or more proteins selected from MAP0196c (SEQ ID NO: 1), MAP0471 (SEQ ID NO: 2) and MAP1981c (SEQ ID NO: 3) is indicative of a MAP infection in the subject. In a preferred embodiment, the presence of one or more proteins selected from MAP1569, MAP0471, MAP3634, and MAP1693c is indicative of a MAP infection in the subject.

In one embodiment, the method comprises detecting the presence or absence of a protein listed in Table 2 in a sample from the subject. In another embodiment, there is provided a method for detecting MAP in a sample comprising testing the sample for the presence or absence of one or more proteins selected from Table 2. In one embodiment, the method comprises testing a sample in vitro for the presence or absence of one or more proteins selected from Table 2. In one embodiment, the method comprises detecting the presence or absence of one or more proteins selected from MAP0471, MAP3634, and MAP1693c. In one embodiment, the sample is a culture filtrate.

In one embodiment, the method comprises determining the presence or absence of MAP3634 in a sample, wherein the presence of MAP3634 is indicative of MAP in the sample. In one embodiment, the method further comprises determining the presence of absence of one or both proteins selected from MAP0471 and MAP1693c, wherein the presence of MAP0471 and MAP1693c is indicative of MAP in the sample. Optionally, the method further includes determining the presence of absence of additional biomarkers for MAP as described herein.

Various assays known in the art for detecting proteins may be used for the methods described herein. For example, in one embodiment the presence or absence of one or more proteins may be determined by contacting the sample with one or more binding proteins that selectively bind to a protein listed in Table 2. In a one embodiment, proteins that are indicative of MAP infection are detected using an ELISA assay, such as with antibodies that selectively bind to one or more of MAP0471, MAP3634, and MAP1693c. The one or more proteins may be detected directly or indirectly, such as by using a labeled secondary antibody to detect the protein of interest.

A person skilled in the art will appreciate that a number of different methods are useful to detect proteins in a sample, including immunoassays such as Western blots, ELISA, and immunoprecipitation followed by SDS-PAGE immunocytochemistry as well as the use or protein arrays (including microarrays) as well as mass spectroscopy.

In some embodiments, the methods described herein use multiplex technology in order to determine the presence of absence of a plurality of proteins listed in Table 2. This technology has the advantage of quantifying multiple proteins simultaneously in one sample.

For example, in one embodiment multiplex technology is used to detect at least two, at least three, at least four or more than four proteins selected from MAP0196c (SEQ ID NO: 1), MAP0471 (SEQ ID NO: 2), MAP1981c (SEQ ID NO: 3), MAP1569 (SEQ ID NO: 4), MAP0281 (SEQ ID NO: 5) MAP1718c (SEQ ID NO: 6), MAP3428c (SEQ ID NO: 7), MAP3634 (SEQ ID NO: 8), MAP2785 (SEQ ID NO: 9), MAP2786c (SEQ ID NO: 10) and MAP1693c (SEQ ID NO: 11).

The following non-limiting examples are illustrative of the present disclosure:

EXAMPLES

Example 1: Secreted Proteins as Biomarkers for *Mycobacterium Paratuberculosis* Infection Johne's disease is a chronic, gastroenteritis of cattle caused by *Mycobacterium avium* subspecies *paratuberculosis* (MAP), and afflicts 40% of dairy herds worldwide. MAP-infected cattle can remain asymptomatic for years while transmitting the pathogen via fecal contamination and milk. Current serodiagnosis by Enzyme Linked ImmunoSorbent Assay (ELISA) fails to detect asymptomatic MAP-infected cattle due to the use of poorly-defined antigens, and knowledge gaps in our understanding of MAP components eliciting pathogen-specific immune responses.

As set out herein, the inventors have defined a subset of proteins that contain putative antigenic targets and, second, screened those antigen pools for immunogens relevant in detecting infection. MAP secreted proteins were captured and resolved using a 2-step fractionation method and reversed-phase liquid chromatography resulting in the identification of 162 unique proteins listed in Table 2, of which 66 had not been previously described as secreted in MAP CF. Subsequent screening of MAP secreted proteins showed four antigens, of which one or more reacted on immunoblotting with individual serum from 35 MAP-infected cows. Moreover, these antigens reacted with sera from 6 low-MAP shedders, and 3 fecal-culture positive cows labeled as ELISA seronegative. The specificity of these antigens was demonstrated using negative control sera from uninfected calves (n=5) and uninfected cows (n=5), which did not react to any of these antigens by immunoblotting.

Materials and Methods
Bacterial Strains and Growth Conditions

MAP strains Madonna, gc86, and gD30 were isolated in our laboratory (December 2001) from the feces of different cows from different dairy herds in Southern Ontario. All three MAP strains were mycobactin J-dependent, PCR (IS900, hspX, ISMAP02, hsp65) positive, and were identified as Cow-type using IS1311. *Mycobacterium avium* subsp. *hominissuis* strain 104 (MAH) and MAP were cultured as static cultures at 37° C. for 4 or 8 weeks, respectively, in Watson-Reid medium, pH 6.0, supplemented with 2 mg/L mycobactin J, 4.1 g/L sodium pyruvate, and 0.075 g/L ferric ammonium citrate (17).

MAP cultures were initiated by inoculating a 1-mL frozen seedlot containing $10^8$ CFU/mL into 50 mL of Middlebrook 7H9 medium (Difco™) supplemented with 5 g/L glycerol, 1 g/L casitone, OADC, and 2 mg/L mycobactin J. At 4-weeks, cells were harvested by centrifugation and washed with 10 mM PBS, pH 7.2, suspended in 60 mL of Watson-Reid medium, and cultured as mentioned earlier.

Preparation of Culture Filtrate Proteins and Cell Lysates

When harvesting bacterial cells, cultures were supplemented with 1 mM PMSF and 5 mM EDTA, pH 8.0 and chilled on ice for 15 min. Cells were separated from the CF by centrifugation (3000×g, 25 min), and the supernatant passaged through a 0.22 µm PES filter. CF proteins were size-fractionated by sequential ultrafiltration using Amicon™ Ultra-15 Centrifugal filter units of molecular weight cut-off of 50 and 3 kDa (Millipore). The filtered volumes retained on the 50 and 3 kDa membranes, labeled SF1 and SF2, respectively, were dialyzed against 10 mM PBS, pH 7.2. To obtain cellular proteins, the harvested cells were suspended in lysis solution [10 mM PBS, pH 7.2, 1% v/v Tween-20], and placed in screw-capped microfuge tubes containing 0.1 mm zirconia/silica. Tubes were shaken in a Mini-Bead Beater for 8×20 s pulses with 3 min rests on ice. Cellular debris and beads were pelleted by centrifugation, 10 000×g for 10 min, and the whole-cell lysate stored at −20° C. Protein concentration was quantified using a Bicinchoninic Acid Kit (Sigma Aldrich).

1D and 2D SDS-PAGE Analysis

For 1D SDS-PAGE, protein samples were diluted in Laemmli sample buffer, incubated at 95° C. for 7 min, and separated at 90 V in a 12% w/v polyacrylamide gel.

For 2D PAGE, 70 µg each of SF1 and SF2 protein preparations were precipitated as per the ReadyPrep™ 2-D Cleanup Kit instructions (Bio-Rad), and the pellet dissolved in 125 µL of ReadyPrep Sequential Extraction Reagent #3 (Bio-Rad) containing 50 mM dithiothreitol (DTT) and 0.05% w/v bromophenol blue. The sample was used to passively rehydrate a 7 cm Immobilized pH gradient (IPG) strip pH 4-7 (ReadyStrip, Bio-Rad) for 1 h before overlaying with mineral oil and active rehydration for 12 h at 50 V. Isoelectric focusing was conducted in a Bio-Rad Protean IEF Cell at 250 V 1 h, 500 V 2 h, and 4000 V to 25 000 V h with the current set at 50 µA per gel. The IPG strips were stored at −70° C. until needed, or immediately equilibrated in SDS equilibration buffer [6 M urea, 375 mM Tris-HCl, pH 8.8, 2% w/v SDS, 20% v/v glycerol] containing 65 mM DTT in the first 15 min wash, and 68 mM iodoacetamide for 15 min in the second wash. The IPG strips were finally equilibrated in Laemmli running buffer, then sealed onto 10% or 15% w/v polyacrylamide gels using agarose sealing solution [0.05% w/v agarose and 0.002% w/v bromphenol blue in Laemmli buffer], and electrophoresed at 90 V. Gels were silver stained (18) with the following changes: Step 2—wash gel with water for 1.5 h, Step 5—formaldehyde was omitted, and Step 8—reaction was stopped and stored in 1% v/v glacial, acetic acid.

In-Gel Trypsin Digestion

Protein gel slices from 1D or 2D SDS-PAGE were excised using a sterile scalpel blade, and destained with 15 mM potassium ferricyanide and 50 mM sodium thiosulfate in water. Cysteine residues were reduced with 10 mM DTT and alkylated with 55 mM iodoacetamide. Gel slices were dried by vacuum centrifugation before incubating at 37° C. overnight in 0.1 µg of sequencing grade, modified porcine trypsin (Promega™) in 50 mM ammonium bicarbonate buffer. Tryptic peptides were extracted from gel slices by one aqueous wash (50 µL and 10 min bath sonication) followed by two washes with 5% formic acid in 50% ACN (75 µL and bath sonication for 5 min). Samples were reduced to dryness by vacuum centrifugation.

LC-MS/MS

Protein samples were subjected to LC-MS/MS analysis. The digested peptides were loaded onto a 150 µm ID pre-column (Magic C18, Michrom Biosciences) at 4 µL/min and separated over a 75 µm ID analytical column packed into an emitter tip containing the same packing material. The peptides were eluted over 60 min at 300 nL/min using a 0% to 40% ACN gradient in 0.1% TFA using an EASY n-LC nano-chromatography pump operated at room temperature (Proxeon Biosystems, Odense Denmark). The peptides were eluted into an LTQ-Orbitrap hybrid mass spectrometer (Thermo-Fisher, Bremen, Germany) operated in a data dependent mode. The MS was acquired at 60,000 FWHM resolution in the FTMS and MS/MS was carried out in the linear ion trap. Six MS/MS scans were obtained per MS cycle.

Tandem MS/MS spectra were extracted, charge state deconvoluted and deisotoped using BioWorks version 3.3 software. All MS/MS samples were analyzed using Mascot (Matrix Science, London, UK; version 2.3.02) and X! Tandem (www.thegpm.org; version 2007.01.01.1). X! Tandem was set up to search a subset of the NCBInr_20110515 database, and Mascot was set up to search the NCBInr_20110515 database (selected for *paratuberculosis*, unknown version, 4553 entries) assuming the digestion enzyme trypsin. Mascot and X! Tandem were searched with a fragment ion mass tolerance of 0.020 Da and a parent ion tolerance of 0.40 Da. Iodoacetamide derivative of cysteine was specified in Mascot and X! Tandem as a fixed modification, variable modifications specified were pyro-glu, s-carbamoylmethyl cysteine cyclization of the N-terminus, deamidation of asparagine, oxidation of methionine, and acetylation of the N-terminus.

Scaffold (version Scaffold_3.4.7, Proteome Software Inc., Portland, Oreg.) was used to validate MS/MS-based peptide and protein identifications. Peptide and protein identifications were accepted if they could be established at greater than 95.0% probability as specified by the Peptide Prophet or Protein Prophet algorithms, and contained at least 2 identified peptides with Mascot identity scores greater than 45. Proteins that contained similar peptides and could not be differentiated based on MS/MS analysis alone were grouped to satisfy the principles of parsimony.

Proteins were subjected to bioinformatic analyses for putative secretory signal peptides using SignalP (SignalP 4.1), PRED-TAT, and SecretomeP (Secretome P 2.0) programs.

Reversed-Phase LC Analysis

RPLC was performed on a Beckman Coulter ProteomeLab™ PF2D using a C18 reversed-phase column (Aeris Phenonmenex; 3.6 µm, 150 mm×4.6 mm), with a SecurityGuard ULTRA (Phenonmenex) cartridge, operated at 23° C. The mobile phase consisted of a gradient elution of solvent B (0.1% v/v TFA in water), and solvent A (0.1% v/v TFA in ACN). The gradient profile was: 2-4 min 0% B to 20% B, 4-34 min 20% B to 80% B, 34-36 min 80% to 100% B, and 36-37 min 100% B to 0% B at a flow rate of 1.0 mL min$^{-1}$. The injected volume was 200 µL and detection wavelength was 214 nm. Eluate was collected using a FC204 Fraction Collector (Gilson), samples concentrated by vacuum centrifugation and reconstituted in 10 mM PBS, pH 7.2.

Animal Sera

Thirty-five serum samples from MAP-infected cows were used in this study. Fourteen sera collected from culled, MAP ELISA- and fecal-positive animals were obtained from the USDA National Veterinary Services Laboratory. These 14 sera were pooled generating JD-14 serum, and used in immunoblots. Twenty-one serum samples from Holstein cows were matched to fecal culture and serum ELISA (IDEXX Laboratories, Inc.; Table 3). The negative control sera included uninfected calf and ELISA-negative cow sera.

These sera were collected from 2 month-old Holstein calves removed within 24 h of birth and maintained in an animal isolation facility. Sera from uninfected cows were collected from a herd with no reported cases of Johne's disease, and confirmed seronegative by ELISA (IDEXX Laboratories, Inc.).

A 1:1 emulsion of 100 μg of MAP SF1 and SF2 protein, or MAH SF1 and SF2 protein in 10 mM PBS, pH 7.2 and TitreMax™ gold adjuvant (Sigma-Aldrich) was injected intramuscularly into eight Sprague-Dawley rats. Four subsequent immunizations consisted of 50 μg of protein and heat-inactivated MAP or MAH cells emulsified in Freund's incomplete adjuvant were administered biweekly. Heat-inactivated cells were prepared by harvesting 1 mL of a MAP or MAH log-phase culture by centrifugation and heat-killing at 80° C. for 30 min. Four days following the last immunization rats were euthanized and whole blood collected for serum preparation.

Immunoblotting

Proteins electrophoresed either by 1D or 2D SDS-PAGE, as described above, were transferred to nitrocellulose membranes (BioTrace NC; Pall) using a semi-dry blotting device (Trans-Blot Turbo Transfer System, Bio-Rad) for 30 min at 10 V and 100 mA. When stated, membranes were subjected to periodate oxidation as described (19). Membranes were blocked in PBS containing 0.05% v/v Tween-20 (PBS-T) and 5% w/v milk powder (Oxoid) for 2 h at room temperature, and incubated in primary antibody diluted in PBS-T-1% milk powder (1:1000 rat antiserum, 1:100 bovine serum) overnight at 15° C. Membranes were rinsed twice, and washed 3 times for 10 min in PBS-T after the primary and secondary antibody incubations. Membranes were incubated in secondary antibody (either 1:3500 rabbit anti-bovine IgG, HRP-conjugated or 1:7500 rabbit anti-rat IgG, HRP conjugated; Sigma-Aldrich) diluted in PBS-T-1% milk powder for 1.5 h at room temperature. Visualization of protein bands reactive to various antisera was performed as described (20).

Results

MAP CF Secretome Analysis

LC-MS/MS analysis was used to characterize the protein profile of the SF1 and SF2 preparations of MAP CF. A total of 162 unique proteins were identified in the three MAP strains, 81 in SF1 and 89 in SF2 (Table 2). Among these, 66 proteins (27 in SF1 and 39 in SF2) are considered by the inventors to be novel proteins. The distribution of hypothetical and annotated proteins varied greatly with 19.7% and 60% hypothetical in SF1 and SF2, respectively. Live-dead staining with fluorescein diacetate and ethidium bromide revealed no dead cells after 8 weeks of incubation (data not shown). Using bioinformatic tools, 28% of the 162 CF proteins, and 34% of the novel proteins, were predicted to contain a canonical secretory peptide for protein export via the general secretion pathway or the twin-arginine translocation system (FIGS. 6A and 6B). The 2D PAGE analysis using various IPGs revealed the majority of proteins as having an isoelectric point between 4-7 (data not shown). This result is consistent with previous findings showing *mycobacterial* secreted proteins are more acidic than cellular proteins (14, 21).

Immunogen Screening of SF1 and SF2 Preparations

Based on the protein concentration and 1D SDS-PAGE analysis, MAP strains secrete a greater abundance and heterogeneity of proteins than MAH (FIG. 1A). This observation is consistent with yields obtained for MAP and MAH for purified protein derivatives (22). Two complementary approaches were used to screen for immunogenic proteins in the SF1 and SF2 preparations. The first approach used polyclonal rat antisera, and the second, the JD-14 serum. Polyclonal rat anti-MAP antibodies exhibited cross-reactivity against antigens in the whole-cell lysates, and SF1 and SF2 preparations of both MAP and MAH (FIG. 1B). Interestingly, the sera showed relatively higher reactivity with homologous low molecular weight (<26 kDa) antigens in the MAP SF1 and SF2 preparations. In comparison, the polyclonal rat anti-MAH antibodies recognized fewer antigens in both MAH and MAP whole-cell lysates and SF1 preparations, and only a single antigen in the MAP SF2 preparation (FIG. 1C). To identify antigens relevant to MAP infection, JD-14 serum was used to screen the same set of antigen pools. Whole-cell lysates and the SF1 preparation of both MAP and MAH showed similar antigenic profiles (FIG. 1D). In contrast, the MAP SF2 preparation contained a number of immunoreactive proteins that were absent in MAH SF2. The MAP SF2 preparation was chosen for subsequent analysis and epitope screening.

Figure 2:
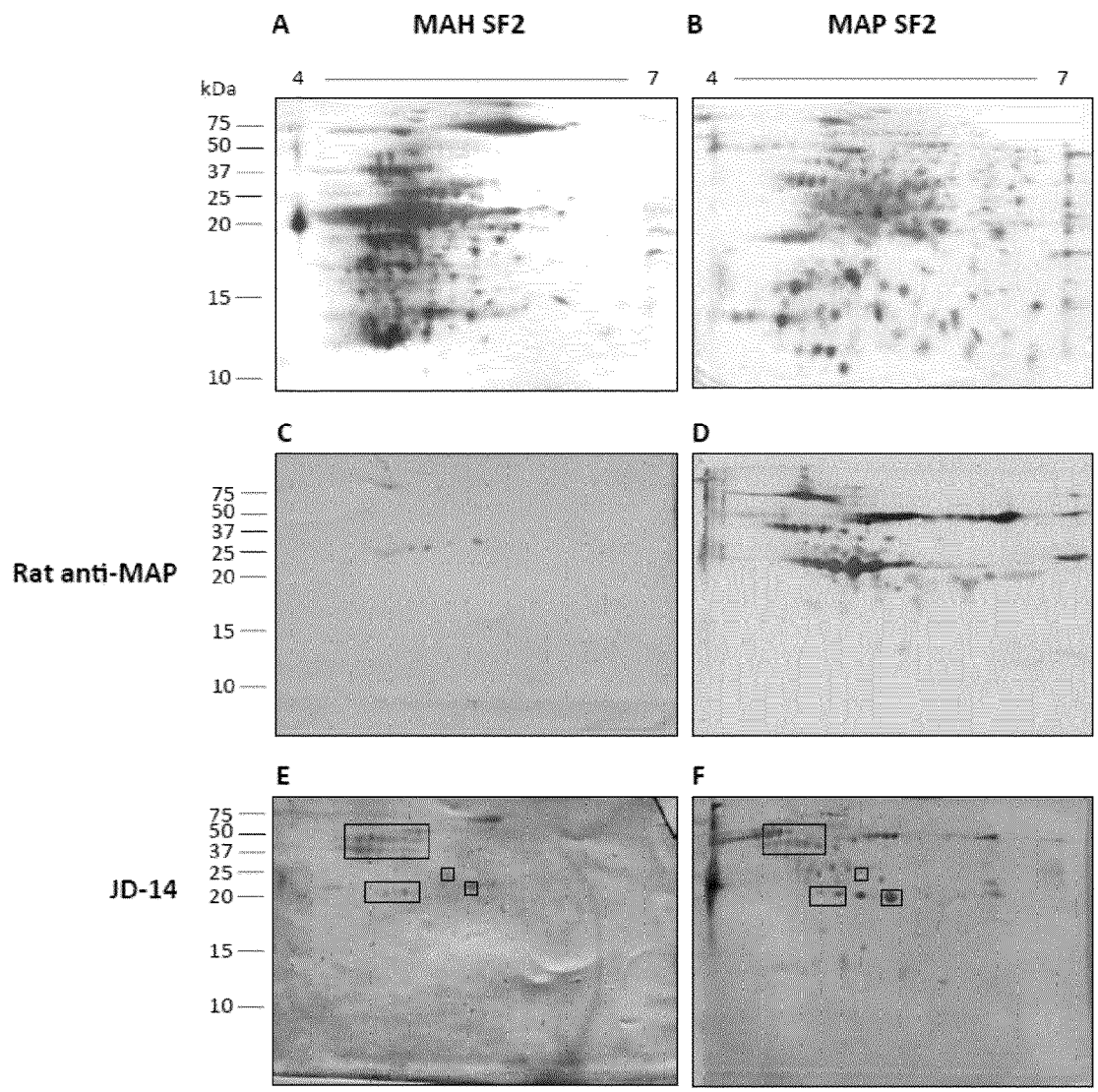
FIG. 2 shows comparative 2D PAGE and immunoblots of MAH SF2 (A, C, E), and MAP SF2 (B,D,F) proteins. Silver-stained 2D PAGE of MAH SF2 (A) and MAP SF2 (B) focused over pH 4-7, and resolved on 15% w/v polyacrylamide gels. Corresponding immunoblots of MAH SF2 (C, E), MAP SF2 (D, F) proteins reacted with polyclonal rat anti-MAP sera (C, D), or JD-14 serum (E, F). Boxes in (E) and (F) denote immunoreactive protein spots common to MAH and MAP, respectively. Molecular weight standards are listed.
Figure 7:
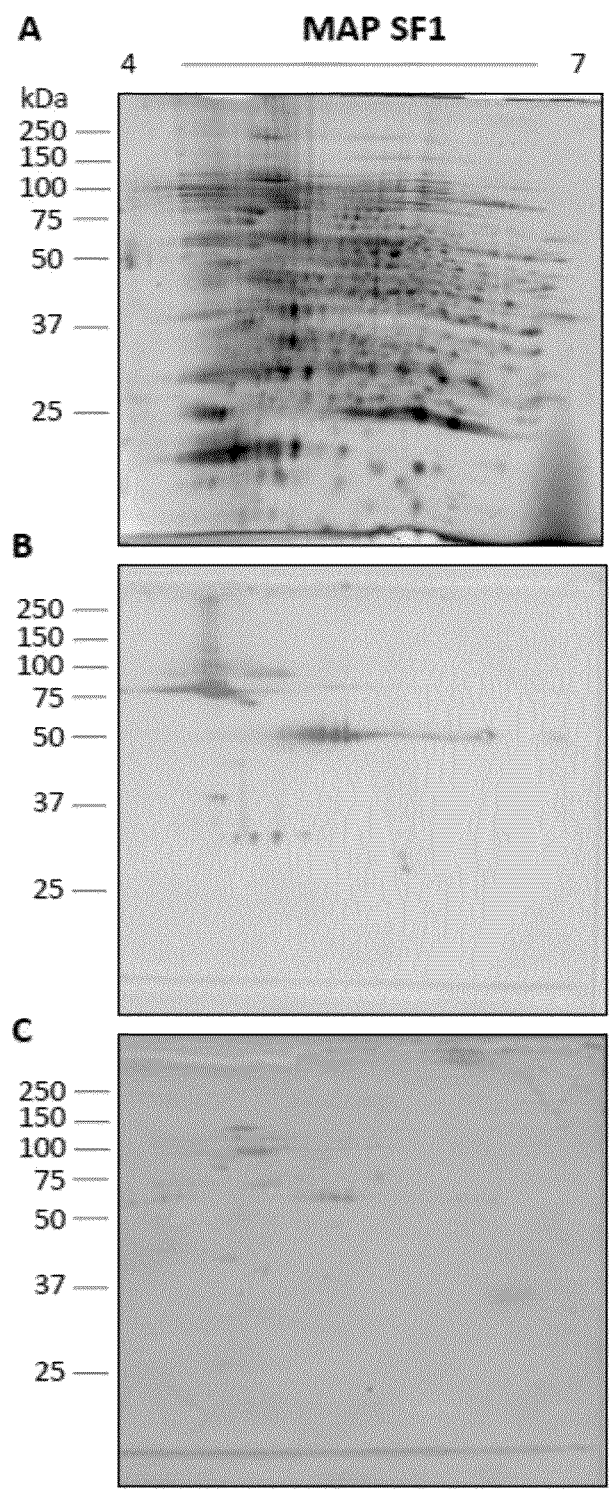
FIG. 7 shows 2D PAGE and immunoblot of MAP SF1 proteins. (A) Seventy µg of total protein was focused over a pH of 4-7, and separated by molecular weight on a 15% w/v polyacrylamide gel. Polyclonal rat anti-MAP serum (B) and JD-14 serum (C) reacted with MAP SF1 proteins. Molecular weight standards are listed.

A comparison of MAH SF2 and MAP SF2 proteins separated by 2D PAGE showed subspecies distinct secreted protein profiles (FIGS. 2A and 2B). In agreement with 1D immunoblotting, 2D immunoblotting with polyclonal rat anti-MAP sera (FIGS. 2C and 2D) and the JD-14 serum (FIGS. 2E and 2F) reacted strongly with MAP SF2 antigens (2D, 2F) in comparison with the MAH antigens (2C, 2E). The JD-14 serum had a significantly lower staining intensity. Both sera detected a few cross-reactive antigens present in MAH SF2 (FIGS. 2C and 2E). Nearly identical reactivity profiles were observed for polyclonal rat anti-MAP and JD-14 serum towards MAP SF1; however, the number of antigens and the intensity of reaction were significantly less compared to MAP SF2 (FIG. 7). Taken together these data suggest that antibodies in sera from naturally MAP-infected cattle and immunized rats are detecting MAP-specific antigens in the MAP SF2 preparation.

Figure 3:
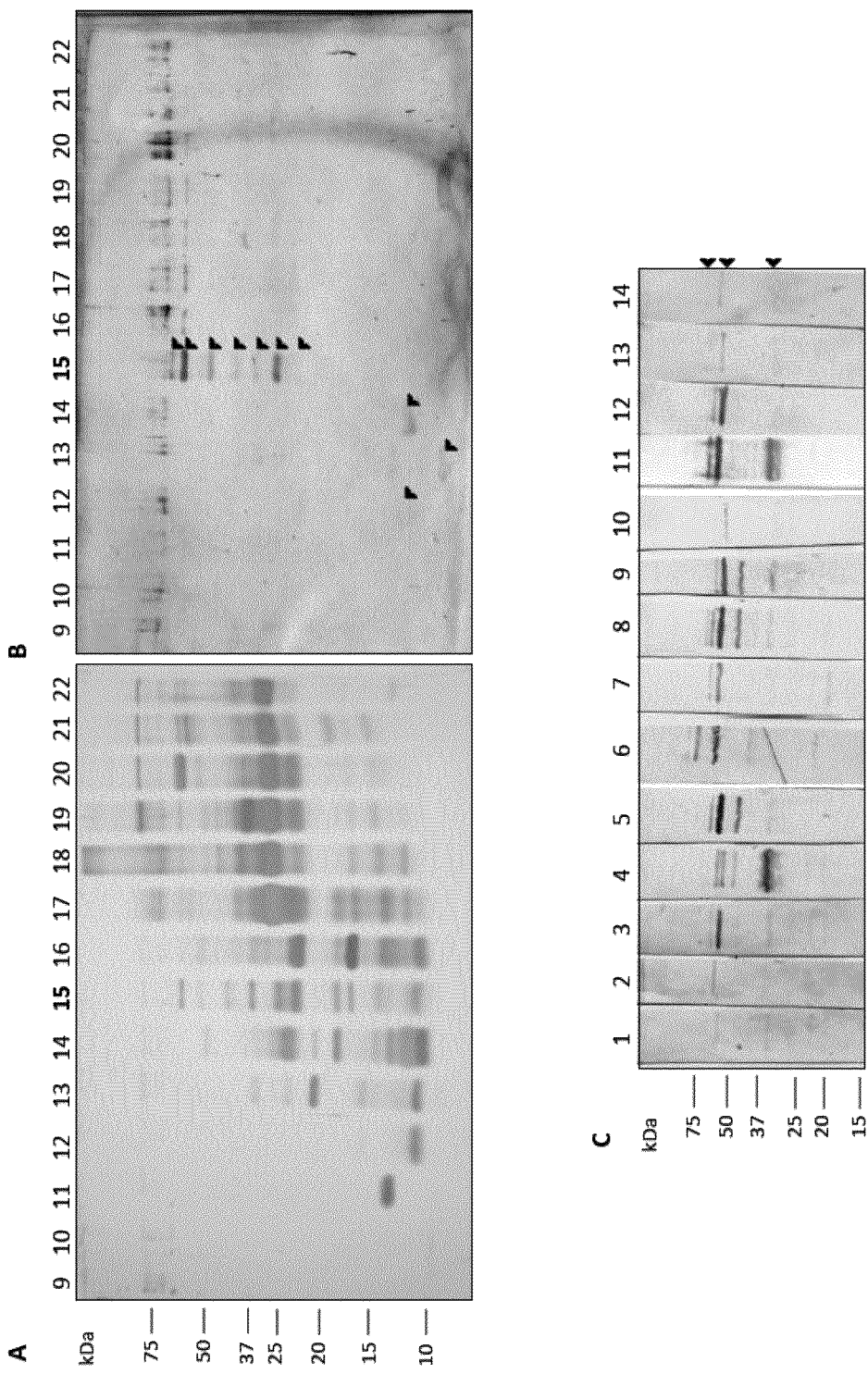
FIG. 3 shows the RPLC fractionation of MAP SF2 proteins. Silver-stained 10 SDS-PAGE showing protein profile of each of the 14 fractions derived from fractionating 200 µg of MAP SF2 protein (A), and corresponding immunoblot reacted with JD-14 serum (B) with arrowheads highlighting all immunoreactive bands. Serum from 14 naturally MAP-infected cows reacted against the F15 proteins (C). Arrowheads in (C) denote the three most frequently recognized antigen-bands. Molecular weight standards are listed.

In-gel digestion of 16 reactive spots from 2D PAGE gave rise to multiple identifications per spot during MS/MS analysis. To better identify the immunoreactive proteins, the MAP SF2 preparation was subjected to RPLC, 1-mL eluate fractions collected, and proteins concentrated and resolved by 1D SDS-PAGE (FIG. 3A). At least 10 antigen bands were identified by immunoblotting with JD-14 serum; 1 each in fractions 12, 13, and 14, and 7 in fraction 15 (F15; FIG. 3B). Immunoblotting of F15 proteins was performed with each of the 14 serum samples comprising the JD-14 serum (FIG. 3C). All 14 serum samples reacted with one or more of the F15 proteins, of which three antigens of apparent molecular sizes of 52 kDa, 47 kDa, and 28 kDa were the most frequently recognized (FIG. 3C).

Figure 4:
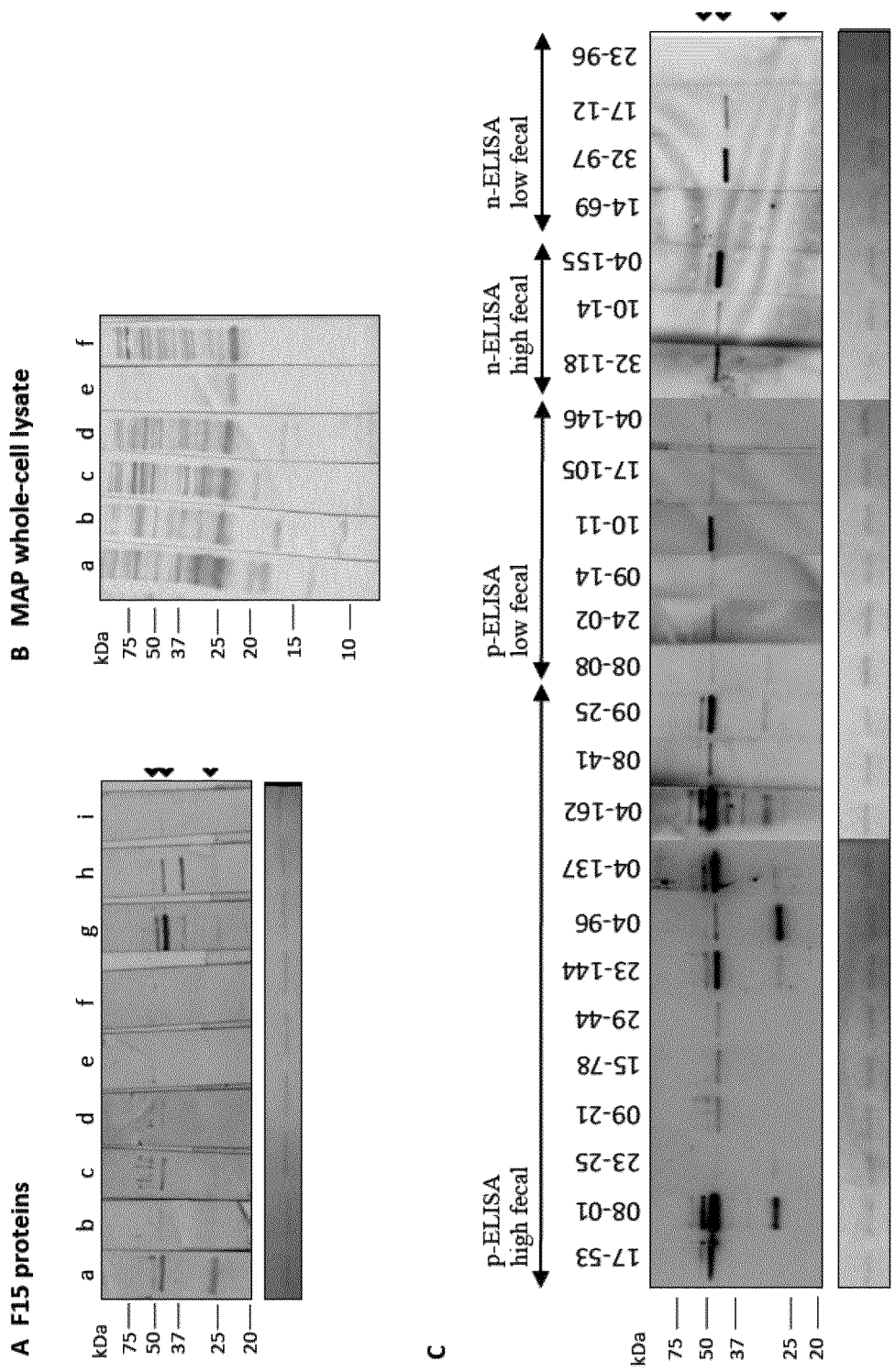
FIG. 4 shows the reactivity of bovine serum from MAP-infected and uninfected cows to the F15 proteins. (A) Immunoblot of the F15 proteins reacted with pooled sera from: (a) p-ELISA/high fecal, (b) p-ELISA/low fecal, (c) n-ELISA/high fecal, (d) n-ELISA/low fecal, (e) uninfected calves, (f) uninfected cows, (g) JD-14 serum, (h) rat anti- MAP sera, and (i) rat anti-MAH sera. P-ELISA and n-ELISA denote ELISA positive or negative, respectively. (B) Immunoblot of pooled sera, tested above, reacted against MAP whole-cell lysates. (C) Individual testing of serum samples belonging to each of the ELISA/fecal groups. Ponceau S staining, shown below immunoblots, confirms equal loading. Arrowheads denote the three most frequently recognized antigen-bands. Molecular weight standards are listed.

To test the potential of F15 proteins as diagnostic reagents we separated the cow sera (n=25) into 4 groups based on the matched IDEXX ELISA test reading, and MAP CFU per gram of feces (Table 3). Sera from p-ELISA/high fecal, p-ELISA/low fecal, n-ELISA/high fecal, and n-ELISA/low fecal, where "p-ELISA" and "n-ELISA" denote seropositive or seronegative, respectively were pooled. The pooled sera, along with positive and negative control sera, were reacted with F15 antigens (FIG. 4A). Unlike commercial ELISA tests, the cow sera in this study were not preabsorbed with environmental *Mycobacterium* or *E. coli* whole-cells or lysates to remove antibodies to shared antigenic epitopes. The order of seroreactivity to F15 proteins as determined by immunoblotting ranked from highest to lowest was: p-ELISA/high fecal>n-ELISA/high fecal>p-ELISA/low fecal>n-ELISA/low fecal (FIG. 4A, panels a,c,b,d, respectively). The individual serum in each pool was reacted with F15 proteins. Antibodies against at least one of the 3 most frequently recognized antigens were detected (FIG. 4C). Based on these data, F15 correlates better with fecal shedding than the test ELISA values.

To address the specificity of these antigens, the unabsorbed pooled sera from 2 month-old calves (n=5), and MAP fecal-culture and ELISA negative cows (n=5) from a Johne's disease-free herd were reacted against the F15 proteins. No antibodies against these proteins were detected in either of these serum samples (FIG. 4A, panels e and f). In contrast, the positive control JD-14 serum reacted with at least 6 proteins (FIG. 4A, panel g). Polyclonal rat MAP-antibodies reacted with only two F15 proteins; polyclonal rat anti-MAH antibodies weakly reacted with only one (FIG. 4A, panels h and i). With the exception of sera from the neonatal calves, all cow sera reacted with multiple antigens in MAP whole-cell lysates (FIG. 4B). These data demonstrate the lack of specificity of MAP whole-cell lysates and the specificity of the F15 antigens.

In-gel digestion of the three most frequently recognized antigens from 1D and 2D gels revealed the 52 kDa antigen-band as MAP0196c, the 42 kDa antigen-band consisted of 2 co-migratory proteins (MAP1569/ModD and MAP0196c), and the 28 kDa antigen-band consisted of two co-migratory proteins (MAP0471 and MAP1981c). BlastP analyses of these four antigens identified similar proteins in *M. avium*, *M. tuberculosis*, *M. bovis*, and *M. leprae* (Table 1). FASTA sequence comparison of the MAP and *M. bovis* proteins revealed amino acid identities ranging from 74-94%. However, comparison of these proteins from MAP and *M. bovis* revealed very few shared, antigenic epitopes were predicted by Bebipred B-cell epitope prediction. MAP0196c, MAP0471, and MAP1981c have been annotated as hypothetical proteins in the MAP genome. MAP1569/ModD is a fibronectin-attachment protein, and has previously been reported as a B-cell antigen (23).

DISCUSSION

Using a 2-step size-fractionation method to capture and concentrate MAP CF proteins, 162 unique proteins were identified; 66 of these have not been previously reported in MAP CF. The use of this methodology was compared to trichloroacetic acid precipitation and single size-fractionation (data not shown). 1D SDS-PAGE analyses revealed distinct protein profiles for each method with the 2-step size fractionation method yielding a higher concentration and heterogeneous protein profile. This two-step methodology likely helped contribute to the successful identification of these previously unreported proteins.

Of the 162 unique proteins identified in this study, only 28% were predicted to contain a canonical secretory peptide. This low value is consistent with extracytoplasmic proteome analyses of MAP and other *Mycobacterial* species. Previous analysis of MAP CF using a polyacrylamide gel-based proteomic approach identified 125 unique proteins of which 28% contained a putative secretory peptide (24). Analysis of the MAP cell-wall proteome by He et al. identified 309 unique proteins where 6% and 50% of cell-wall localized and surface-exposed proteins, respectively, were predicted to contain a secretory signal peptide (25). In other studies, bioinformatic analysis of the *M. tuberculosis* genome had predicted only 52 out of the 3924 ORFs to contain a secretory signal peptide, in contrast to the over 250 proteins identified in CF studies (26, 27). Comparative analyses of whole-cell lysates and CF proteins using 2D PAGE found a significant overlap (45%) between these subproteomes, and only 31% of the 137 CF proteins were predicted to contain a secretory signal peptide (21). One group has reported purifying *M. tuberculosis* CF proteins with 62% predicted to contain a secretory signal peptide, but attributed strain differences as the source of disparity between their observations and that previously reported (27).

There are two possible explanations for why such a small percentage of Mycobacterial proteins are assigned a predictable secretory peptide. The first extends from the lack of data regarding signaling components necessary to orchestrate the translocation of proteins across the cell wall, and the second can be attributed to the phenomenon of moonlighting proteins. To date, three secretion systems have been identified in *Mycobacteria*: SecA1/SecA2, Tat, and the Type VII secretion system (28). Canonical signals are well characterized for SecA1 and Tat, but it is only recently that conserved motifs have been identified for the Type VII secretion system (29). With limited understanding of secretion signals in *mycobacteria*, further confounded by the complexity of mycobacterial cells walls, one may speculate that there remains unidentified signal peptides in combination with additional translocation mechanisms that may explain the export of these unaccounted for secreted proteins not falling with the Sec/Tat/Type VII pathways. The second confounding factor in defining a secreted protein arises from their dual localization. A significant amount of data has accumulated to support dual localization of prokaryotic (and eukaryotic) cytoplasmic proteins termed "moonlighting proteins" for their ability to coexist in two subcellular compartments while carrying out diverse roles in each location (30). This phenomenon has been identified in *Mycobacteria, Listeria, Neisseria, Staphylococcus, Streptococcus, Helicobacter*, and *Franciscella* (31). Some of the functions assigned to these moonlighting proteins, to date, is their capacity to mediate host-cell adhesion, modulate macrophage cytokine secretion, and control of gene expression through secretion of transcriptional regulators (32-34). Taken together, extracellular protein localization is still limited to empirical methods of detection as non-canonical translocation systems, especially in *Mycobacteria*, remain poorly understood. Moreover, one cannot always preclude the localization of a protein based on its prior localization or annotation. Secretion of these unusual proteins therefore appears to be a true phenomenon and portrays the extraordinary plasticity of proteins.

The 162-protein secretome defined in this study was compared to three MAP cellular proteomes containing both cytoplasmic- and membrane-enriched protein fractions (35-37). A total of 130 proteins overlapped with the cytoplasmic protein fractions from MAP cells cultured in vitro (35, 37); 54 proteins overlapped with the membrane-enriched protein fractions (35, 36). The proteins overlapping in these studies included both previously described moonlighting proteins, and proteins reported in the CF of *Mycobacteria* (i.e. DnaK, Antigen-85, eIF-Tu, malate synthase G, and isocitrate lyase) (31, 38). 117 proteins from the in vitro secretome were also identified from MAP cytoplasmic (total 938 proteins) and membrane-enriched (total 325 proteins) protein fractions obtained from mucosal scrapings of bovine ileum tissue (36, 37). Similarly, a comparative analysis was conducted against the MAP K10 cell-wall proteome. A total of 309 proteins were identified with only 23 proteins found to overlap (25). These data suggest that the methodologies employed in the cytoplasmic proteome, cell wall proteome, and secretome defined in the present example are indeed isolating and enriching unique MAP subproteomes as evidenced by the small overlap in protein identities in comparison to the total number of proteins identified in each proteomic dataset.

One of the current challenges in Johne's disease management is Identifying MAP-specific components that can be exploited for diagnostic value. This challenge arises from T- and B-cell epitope cross-reactivity from environmental exposure to closely related Mycobacteria, such as those belonging to the Mycobacterium avium complex. MAH shares 95% nucleotide sequence identity to MAP across 3241 of 3497 ORFs analyzed (39). For diagnostic purposes, comparative analysis to MAH is of paramount importance in determining and eliminating cross-reactive epitopes. Using the rat model, it was determined that MAH CF-immunized serum cross-reacted with only a few antigens in the MAP SF2 preparation. In contrast, MAP CF-immunized serum reacted strongly and extensively with these same antigens. These data suggest that exposure to MAH, or other closely related Mycobacteria, may not be problematic towards generating cross-reactive antibodies against these particular antigens. Moreover, antibodies against the 3 most frequently recognized F15 antigens were detected in serum from MAP-infected cows, but only one of these antigen reacted with serum from MAP-immunized rats. Determining whether antibodies against these antigens are generated in cows that have been immunized with MAP CF protein may help further distinguish antigens relevant to infection versus immunization.

As the SF2 preparation contained putative MAP-specific antigens, this fraction was subjected to further immunogen analyses. As MAP material is often obtained in low amounts, RPLC facilitated concentration with minimal loss, and aided in high-throughput analysis by 1D SDS-PAGE by reducing sample complexity. This methodology yielded a different reactive profile than 1D immunoblotting, and aided in the identification of a different set of antigens not identified using only 1D or 2D immunoblotting. The RPLC fractionation of MAP SF2 led to the identification of at least 10 seroreactive antigens not identified in the 1D immunoblot of the unfractionated SF2 preparation. These findings underline the importance of applying various methodologies beyond 1D and 2D immunoblotting in antigen screening experiments.

A comparative study of serum ELISA to MAP-fecal shedding reported that the sensitivity of commercial ELISAs strongly correlated with the number of MAP shed in feces (10). The lowest sensitivity of 5% was evidenced in low MAP-shedders (less than 10 CFU cultured), and increased to 88% in high MAP-shedders (greater than 40 CFU cultured). The dependence of increased sensitivity with fecal shedding provides an inherent limitation in detecting the subset of early and subclinical infected animals that are most often categorized as low MAP shedders. The present example provides evidence suggesting that MAP F15 antigens are superior to that of commercial ELISA antigens as they are not limited in their capability to detect low- and high-MAP shedders. Serum from 3 high-shedding seronegative cows, and 6 low-shedding (less than 7 CFU cultured) seropositive cows reacted with at least one of the three most frequently recognized antigen-bands in MAP F15. In contrast to commercial ELISAs, the set of F15 antigens including MAP0196c, MAP0471, MAP1981c and MAP1569 correctly identified all 9 samples as seropositive. Furthermore, pre-absorption of serum (as required for commercial ELISAs) was dispensable, as reactivity to MAP F15 antigens was evident only in serum from MAP-infected animals, and not from negative control animals. In contrast, all sera reacted extensively with MAP cell lysates further supporting the notion that MAP F15 antigens are useful for differentiating infected from uninfected animals.

Bioinformatic analyses of MAP0196c, MAP0471, MAP1981c and MAP1569 revealed proteins of high sequence similarity belonging to other *Mycobacterial* species including those found ubiquitously in the environment, such as MAH (Table 1). Although the negative control serum was obtained from JD ELISA- and fecal-negative animals, the sera reacted strongly with MAP cell lysates. These data suggest that these uninfected animals were exposed to shared epitopes belonging to environmental *Mycobacterium*. However, these serum samples did not cross-react with MAP F15 proteins by immunoblotting suggesting that epitope determinants belonging to these four antigens, although containing highly homologous counterparts in other *Mycobacterium*, may elicit a unique immunological response in the context of MAP infection. This pathogen-mediated response to these proteins facilitates the use of these antigens in discriminating infected from uninfected animals.

The inventors have identified novel antigens that can be used to expand the diagnostic tool kit for Johne's disease. Four MAP proteins were identified that uniquely reacted with serum from MAP-infected cows. In addition, sera from low MAP shedders (<10 CFU) also reacted with at least one of these antigens. The specificity of these proteins was demonstrated by: calf and uninfected cow sera containing no detectable antibodies to these antigens, and not having to resort to serum preadsorption to remove antibodies to common antigens. These proteins represent useful biomarkers for the detection of MAP infections and the use of these antigens in an ELISA-based format may aid in the immediate management of Johne's disease by detecting those animals shedding low CFUs of MAP, which current commercial serum ELISA tests fail to do.

TABLE 1

Comparative bioinformatic analysis of the 4 MAP antigens to Mycobacterial homologs of pathogenic and diagnostic value.

| MAP Gene ID | Pfam Domain | kDa | *M. avium* 104 | *M. bovis* AF2122/97 | M. tb H37Rv | *M. leprae* TN | Common Epitopes MAP v *M. bovis* |
|---|---|---|---|---|---|---|---|
| 1569 | FAP | 36 | Mav2859 95% | Mb1891 74% | Rv1860 74% | ML2055 74% | 2/12 |
| 0471 | Shisa | 28 | Mav0566 99% | Mb3618c 94% | Rv3587C 94% | ML1918 90% | 2/7 |
| 1981c | DUF164 | 27 | Mav2210 99% | Mb2254c 90% | Rv2229c 90% | ML1638 80% | 1/7 |

TABLE 1-continued

Comparative bioinformatic analysis of the 4 MAP antigens to
Mycobacterial homologs of pathogenic and diagnostic value.

| MAP Gene ID | Pfam Domain | kDa | M. avium 104 | M. bovis AF2122/97 | M. tb H37Rv | M. leprae TN | Common Epitopes MAP v M. bovis |
|---|---|---|---|---|---|---|---|
| 0196c | Septum_form | 46 | Mav0192 98% | Mb3865 81% | Rv3835 81% | ML0081 83% | 1/15 |

Standard Protein BLAST was used to search for Mycobacterial homologs, and subsequently analyzed for percent similarity using FASTA sequence comparison. Bioinformatic prediction of common B-cell epitopes was performed for MAP homologs in *M. bovis* using the Bepipred Linear Epitope Prediction (IEDB Analysis Resource). Data is presented as total number of common epitopes over the total number of MAP epitopes predicted; only epitopes 4 or more amino acids in length were considered.

TABLE 2

CF Proteins identified in MAP SF1 and SF2 preparations. GO terms
were retrieved from the protein information resource database.

| Protein Name | MAP Gene # | Accession Number | Mol. Weight | GO Term | SF1 | SF2 |
|---|---|---|---|---|---|---|
| DNA polymerase III subunit beta | MAP0002 | gi\|41406100 | 42 kDa | DNA replication | Y | |
| PpiA; peptidyl-prolyl cis-trans Isomerase A | MAP0011 | gi\|41406109 | 19 kDa | Protein modification process | | Y |
| hypothetical protein | MAP0023c | gi\|41406121 | 59 kDa | None | | Y |
| hypothetical protein | MAP0030c | gi\|41406128 | 12 kDa | None | | Y |
| single-strand DNA-binding protein | MAP0068 | gi\|41406166 | 18 kDa | DNA replication | Y | |
| FadE25_2 | MAP0150c | gi\|41406248 | 44 kDa | Metabolic Process | Y | |
| hypothetical protein | MAP0151c | gi\|41406249 | 17 kDa | None | | Y |
| hypothetical protein | MAP0187c | gi\|41406285 | 23 kDa | Metabolic Process | Y | |
| prephenate dehydratase | MAP0193 | gi\|41406291 | 33 kDa | Metabolic Process | Y | |
| FbpC1 | MAP0217 | gi\|41406315 | 31 kDa | None | | Y |
| Pks13; polyketide synthase 13 | MAP0220 | gi\|41406318 | 191 kDa | Metabolic Process | Y | |
| hypothetical protein | MAP0262 | gi\|41406360 | 58 kDa | None | Y | |
| hypothetical protein | MAP0301 | gi\|41406399 | 25 kDa | Metabolic Process | | Y |
| 2-isopropylmalate synthase | MAP0312 | gi\|161611210 | 55 kDa | amino acid metabolism process | Y | |
| hypothetical protein | MAP0318 | gi\|41406416 | 27 kDa | Polysaccharide Metabolic Process | | Y |
| hypothetical protein | MAP0333 | gi\|41406431 | 21 kDa | Metabolic Process | | Y |
| hypothetical protein | MAP0343 | gi\|41406441 | 14 kDa | None | | Y |
| hypothetical protein | MAP0467c | gi\|41406565 | 12 kDa | None | | Y |
| LpqE | MAP0474c | gi\|41406572 | 19 kDa | None | | Y |
| hypothetical protein | MAP0534 | gi\|41406632 | 11 kDa | None | | Y |
| hypothetical protein | MAP0586c | gi\|41406684 | 33 kDa | None | | Y |
| hypothetical protein | MAP0593c | gi\|41406691 | 15 kDa | Metabolic Process | | Y |
| adenylosuccinate lyase | MAP0611 | gi\|41406709 | 51 kDa | Nucleotide Metabolic Process | Y | |
| hypothetical protein | MAP0630c | gi\|41406728 | 29 kDa | Response to Stimulus | Y | |
| DesA1 | MAP0658c | gi\|41406756 | 39 kDa | Oxidation-reduction process | Y | |
| Fad B_1 | MAP0790 | gi\|41406888 | 76 kDa | Lipid metabolic process | Y | |
| hypothetical protein | MAP0796c | gi\|41406894 | 11 kDa | None | | Y |
| SerC, phosphoserine aminotransferase | MAP0823c | gi\|41406921 | 40 kDa | Amino acid metabolic process | Y | |
| CitA; citrate synthase 2 | MAP0827c | gi\|41395275 | 42 kDa | Carbohydrate metabolic process | Y | |
| Type II citrate synthase | MAP0829 | gi\|41406927 | 48 kDa | Carbohydrate metabolic process | Y | |

TABLE 2-continued

CF Proteins identified in MAP SF1 and SF2 preparations. GO terms were retrieved from the protein information resource database.

| Protein Name | MAP Gene # | Accession Number | Mol. Weight | GO Term | SF1 | SF2 |
|---|---|---|---|---|---|---|
| hypothetical protein | MAP0834c | gi\|41406932 | 25 kDa | Cell communication | | Y |
| glucose-6-phosphate isomerase | MAP0891c | gi\|41406989 | 61 kDa | Carbohydrate metabolic process | Y | |
| formyltransferase | MAP0903 | gi\|41407001 | 57 kDa | Metabolic Process | Y | |
| hypothetical protein | MAP0904 | gi\|41407002 | 25 kDa | None | | Y |
| hypothetical protein | MAP0907 | gi\|41407005 | 31 kDa | Oxidation-reduction process | | Y |
| hypothetical protein | MAP0918 | gi\|41407016 | 48 kDa | Proteolysis | | Y |
| methionyl-tRNA synthetase | MAP0972c | gi\|41407070 | 59 kDa | Translation | | Y |
| ribose-phosphate pyrophosphokinase | MAP0983c | gi\|41407081 | 35 kDa | Nucleoside Metabolic Process | Y | |
| enoyl-CoA hydratase | MAP1017c | gi\|41407115 | 28 kDa | Metabolic Process | Y | |
| enoyl-CoA hydratase | MAP1018c | gi\|41407116 | 37 kDa | Metabolic Process | | Y |
| transcription elongation factor GreA | MAP1027c | gi\|41407125 | 18 kDa | Transcription Elongation | | Y |
| MIHF | MAP1122 | gi\|41407220 | 12 kDa | None | | Y |
| glyceraldehyde-3-phosphate dehydrogenase | MAP1164 | gi\|41407262 | 36 kDa | carbohydrate metabolic process | Y | |
| phosphoglycerate kinase | MAP1165 | gi\|41407263 | 42 kDa | carbohydrate metabolic process | | Y |
| triosephosphate isomerase | MAP1166 | gi\|41407264 | 28 kDa | carbohydrate metabolic process | | Y |
| 6-phosphogluconolactonase | MAP1174c | gi\|41407272 | 26 kDa | carbohydrate metabolic process | | Y |
| transaldolase | MAP1177c | gi\|41407275 | 40 kDa | carbohydrate metabolic process | | Y |
| transketolase | MAP1178c | gi\|41407276 | 75 kDa | Metabolic Process | Y | |
| hypothetical protein | MAP1196 | gi\|41407294 | 13 kDa | Regulation of biological process | | Y |
| aconitate hydratase | MAP1201c | gi\|161611206 | 102 kDa | Metabolic Process | Y | |
| MutA; methylmalonyl-CoA mutase | MAP1225 | gi\|41407323 | 66 kDa | Metabolic Process | Y | |
| methylmalonyl-CoA mutase | MAP1226 | gi\|41407324 | 81 kDa | Metabolic Process | Y | |
| isoleucyl-tRNA synthetase | MAP1246 | gi\|41407344 | 118 kDa | Translation | Y | |
| hypothetical protein | MAP1272c | gi\|41407370 | 33 kDa | None | | Y |
| N-acetyl-gamma-glutamyl-phosphate reductase | MAP1361 | gi\|41407459 | 35 kDa | Amino acid metabolism | Y | |
| Ornithine carbamoyltransferase | MAP1365 | gi\|41407463 | 34 kDa | Amino acid metabolism | Y | |
| argininosuccinate synthase | MAP1367 | gi\|41407465 | 44 kDa | Amino acid metabolism | Y | |
| argininosuccinate lyase | MAP1368 | gi\|41407466 | 50 kDa | Amino acid metabolism | Y | |
| Rieske (2Fe—2S) domain-containing protein | MAP1434 | gi\|41407532 | 44 kDa | Oxidation-reduction process | Y | |
| hypothetical protein | MAP1452c | gi\|41407550 | 32 kDa | None | Y | |
| hypothetical protein | MAP1473c | gi\|41407571 | 20 kDa | None | | Y |
| hypothetical protein | MAP1540 | gi\|41407638 | 17 kDa | None | | Y |
| malate synthase G | MAP1549c | gi\|41407647 | 80 kDa | Carbohydrate metabolic process | Y | Y |
| hypothetical protein | MAP1562c | gi\|41407660 | 13 kDa | None | | Y |
| ModD | MAP1569 | gi\|41407667 | 36 kDa | None | | Y |
| hypothetical protein | MAP1587c | gi\|41407685 | 50 kDa | Carbohydrate metabolic process | | Y |

TABLE 2-continued

CF Proteins identified in MAP SF1 and SF2 preparations. GO terms were retrieved from the protein information resource database.

| Protein Name | MAP Gene # | Accession Number | Mol. Weight | GO Term | SF1 | SF2 |
|---|---|---|---|---|---|---|
| AhpD; alky hydroperoxide reductase subunit D | MAP1588c | gi|41407686 | 19 kDa | Response to Stimulus | Y | |
| hypothetical protein | MAP1589c | gi|41407687 | 22 kDa | Oxidation-reduction process | Y | Y |
| BfrA; bacterioferritin | MAP1595 | gi|41407693 | 18 kDa | Oxidation-reduction process | Y | |
| fibronectin-binding antigen 85 complex B | MAP1609c | gi|41407707 | 35 kDa | None | | Y |
| Isocitrate lyase | MAP1643 | gi|41407741 | 85 kDa | Metabolic Process | Y | |
| hypothetical protein | MAP1659 | gi|41407757 | 26 kDa | None | | Y |
| citrate lyase beta subunit | MAP1688 | gi|41407786 | 24 kDa | Metabolic Process | Y | |
| hypothetical protein | MAP1693c | gi|41407791 | 18 kDa | Protein modification process | | Y |
| hypothetical protein | MAP1717 | gi|41407815 | 22 kDa | None | | Y |
| hypothetical protein | MAP1718c | gi|41407816 | 16 kDa | None | | Y |
| Wag31 | MAP1889c | gi|41407987 | 28 kDa | None | Y | |
| hypothetical protein | MAP1944c | gi|41408042 | 13 kDa | cofactor metabolic process | | Y |
| leucyl aminopeptidase | MAP1953 | gi|41408051 | 53 kDa | Protein metabolic process | Y | |
| dihydrolipoamide acetyltransferase | MAP1956 | gi|41408054 | 61 kDa | Metabolic Process | Y | |
| GlnA1; glutamine synthetase | MAP1962 | gi|41408060 | 54 kDa | amino acid metabolism | Y | |
| GlnA2; glutamine synthetase | MAP1966c | gi|41408064 | 50 kDa | amino acid metabolism | Y | |
| pyruvate dehydrogenase subunit E1 | MAP1994 | gi|41408092 | 103 kDa | Metabolic Process | Y | |
| acyl carrier protein | MAP1997 | gi|41408095 | 12 kDa | Lipid metabolic process | | Y |
| heat shock protein 90 | MAP2069c | gi|41408167 | 73 kDa | Response to Stimulus | Y | |
| hypothetical protein | MAP2123 | gi|41408221 | 32 kDa | amino acid metabolism | Y | |
| hypothetical protein | MAP2131c | gi|41408229 | 20 kDa | Metabolic Process | | Y |
| hypothetical protein | MAP2167c | gi|41408265 | 17 kDa | None | | Y |
| hypothetical protein | MAP2168c | gi|41408266 | 18 kDa | None | | Y |
| valyl-tRNA synthetase | MAP2271c | gi|41408369 | 99 kDa | Translation | Y | |
| trigger factor | MAP2282c | gi|41408380 | 51 kDa | Protein transport | Y | |
| ribose-5-phosphate isomerase B | MAP2285c | gi|41408383 | 17 kDa | carbohydrate metabolic process | | Y |
| hypothetical protein | MAP2286c | gi|41408384 | 23 kDa | None | | Y |
| hypothetical protein | MAP2287 | gi|41408385 | 95 kDa | Proteolysis | Y | |
| hypothetical protein | MAP2432c | gi|41408530 | 96 kDa | carbohydrate metabolic process | Y | |
| hypothetical protein | MAP2435c | gi|41408533 | 31 kDa | Regulation of biological process | | Y |
| Putative pterin-4-alpha-carbinolamine dehydratase | MAP2623 | gi|48428207 | 10 kDa | Aromatic compound metabolic process | | Y |
| enoyl-CoA hydratase | MAP2639 | gi|41408737 | 28 kDa | Metabolic Process | Y | |
| 6-phosphogluconate dehydrogenase-like protein | MAP2670c | gi|41408768 | 36 kDa | carbohydrate metabolic process | Y | |
| fumarate hydratase | MAP2693 | gi|41408791 | 50 kDa | cofactor metabolic process | Y | |
| DesA2; acyl-[acyl-carrier-protein] desaturase | MAP2698c | gi|41408796 | 31 kDa | Oxidation-reduction process | Y | |

TABLE 2-continued

CF Proteins identified in MAP SF1 and SF2 preparations. GO terms
were retrieved from the protein information resource database.

| Protein Name | MAP Gene # | Accession Number | Mol. Weight | GO Term | SF1 | SF2 |
|---|---|---|---|---|---|---|
| Serine hydroxymethyltransferase | MAP2699c | gi\|41408797 | 45 kDa | amino acid metabolism | Y | |
| hypothetical protein | MAP2705c | gi\|41408803 | 14 kDa | None | | Y |
| TesB2; acyl-CoA thioesterase II | MAP2709c | gi\|41408807 | 31 kDa | cofactor metabolic process | Y | |
| hypothetical protein | MAP2723c | gi\|41408821 | 12 kDa | None | | Y |
| hypothetical protein | MAP2746 | gi\|41408844 | 17 kDa | None | | Y |
| hypothetical protein | MAP2770 | gi\|41408868 | 19 kDa | None | | Y |
| hypothetical protein | MAP2785c | gi\|41408883 | 18 kDa | None | | Y |
| PpgK; polyphosphate glucokinase | MAP2819 | gi\|41408917 | 28 kDa | None | | Y |
| hypothetical protein | MAP2837c | gi\|41408935 | 82 kDa | None | | Y |
| hypothetical protein | MAP2860 | gi\|41408958 | 11 kDa | None | | Y |
| polynucleotide phosphorylase/polyadenylase | MAP2891c | gi\|41408989 | 81 kDa | Macromolecule catabolic process | Y | |
| enoyl-CoA hydratase | MAP2904 | gi\|41409002 | 26 kDa | Metabolic Process | Y | |
| ribosome recycling factor | MAP2945c | gi\|41409043 | 21 kDa | Translation | | Y |
| elongation factor Ts | MAP2955c | gi\|41409053 | 29 kDa | Translation | Y | Y |
| glutamyl-tRNA synthetase | MAP3029c | gi\|41409127 | 54 kDa | Translation | | Y |
| hypothetical protein | MAP3061c | gi\|41409159 | 28 kDa | None | | Y |
| hypothetical protein | MAP3152c | gi\|41409250 | 33 kDa | aromatic compound metabolic process | Y | |
| CatB; catalase | MAP3236 | gi\|41409334 | 78 kDa | Metabolic Process | Y | |
| lipoprotein LpqB | MAP3358c | gi\|41409456 | 61 kDa | None | | Y |
| MtrA | MAP3360c | gi\|15866137 | 25 kDa | Response to Stimulus | | Y |
| S-adenosyl-L-homocysteine hydrolase | MAP3362c | gi\|41409460 | 54 kDa | One-carbon metabolic process | Y | |
| hypothetical protein | MAP3385 | gi\|41409483 | 32 kDa | Metabolic Process | | Y |
| AccD5; propionyl-CoA carboxylase beta chain | MAP3399 | gi\|41409497 | 59 kDa | None | Y | |
| hypothetical protein | MAP3402 | gi\|41409500 | 33 kDa | None | | Y |
| AldB; aldehyde dehydrogenase | MAP3413 | gi\|41409511 | 53 kDa | Metabolic Process | Y | |
| hypothetical protein | MAP3428c | gi\|41409526 | 24 kDa | Metabolic Process | | Y |
| isocitrate dehydrogenase | MAP3455c | gi\|41409553 | 46 kDa | cofactor metabolic process | Y | |
| Icd2; isocitrate dehydrogenase | MAP3456c | gi\|41409554 | 83 kDa | cofactor metabolic process | Y | |
| O-acetylhomoserine aminocarboxypropyltransferase fgaminocarboxypropyltransferase | MAP3457 | gi\|41409555 | 48 kDa | amino acid metabolism | Y | |
| hypothetical protein | MAP3495c | gi\|41409593 | 26 kDa | Metabolic Process | | Y |
| FbpC2/Antigen85-C | MAP3531c | gi\|41409629 | 38 kDa | None | | Y |
| hypothetical protein | MAP3567 | gi\|41409665 | 30 kDa | metabolic Process | Y | Y |
| hypothetical protein | MAP3634 | gi\|41409732 | 36 kDa | None | | Y |
| phosphoenolpyruvate carboxykinase | MAP3646 | gi\|41409744 | 68 kDa | carbohydrate metabolic process | Y | Y |
| FadE3_2 | MAP3651c | gi\|41409749 | 44 kDa | Metabolic Process | Y | |
| hypothetical protein | MAP3659 | gi\|41409757 | 54 kDa | Metabolic Process | Y | |
| succinic semialdehyde dehydrogenase | MAP3673c | gi\|41409771 | 50 kDa | Metabolic Process | Y | Y |
| succinate dehydrogenase flavoprotein subunit | MAP3698c | gi\|41409796 | 71 kDa | Oxidation-reduction process | Y | |
| hypothetical protein | MAP3799 | gi\|41409897 | 45 kDa | None | | Y |
| hypothetical protein | MAP3804 | gi\|41409902 | 30 kDa | carbohydrate metabolic process | | Y |

TABLE 2-continued

CF Proteins identified in MAP SF1 and SF2 preparations. GO terms were retrieved from the protein information resource database.

| Protein Name | MAP Gene # | Accession Number | Mol. Weight | GO Term | SF1 | SF2 |
|---|---|---|---|---|---|---|
| molecular chaperone DnaK | MAP3840 | gi\|41409938 | 67 kDa | Response to Stimulus | Y | Y |
| hypothetical protein | MAP3841 | gi\|41409939 | 24 kDa | Response to Stimulus | Y | |
| ScoB; 3-oxoacid CoA-transferase | MAP3861 | gi\|41409959 | 48 kDa | Metabolic Process | Y | |
| hypothetical protein | MAP3872 | gi\|41409970 | 16 kDa | None | | Y |
| chaperonin GroEL | MAP3936 | gi\|41410034 | 57 kDa | protein metabolic process | | Y |
| hypothetical protein | MAP3948c | gi\|41410046 | 13 kDa | None | | Y |
| dihydrolipoamide dehydrogenase | MAP3956 | gi\|41410054 | 46 kDa | Regulation of biological process | Y | |
| hypothetical protein | MAP3977c | gi\|41410075 | 26 kDa | Metabolic Process | Y | |
| pyrroline-5-carboxylate reductase | MAP3991 | gi\|41410089 | 30 kDa | amino acid metabolism | Y | |
| hypothetical protein | MAP4009 | gi\|41410107 | 26 kDa | None | | Y |
| hypothetical protein | MAP4056c | gi\|41410154 | 14 kDa | None | | Y |
| nucleotide-binding protein | MAP4063c | gi\|41410161 | 18 kDa | None | | Y |
| 50S ribosomal protein L7/L12 | MAP4126 | gi\|41410224 | 13 kDa | Translation | | Y |
| elongation factor G | MAP4142 | gi\|41410240 | 77 kDa | Nucleoside Metabolic Process | Y | |
| elongation factor Tu | MAP4143 | gi\|41410241 | 44 kDa | Nucleoside Metabolic Process | Y | Y |
| adenylate kinase | MAP4199 | gi\|41410297 | 20 kDa | phosphorus metabolic process | | Y |
| MmsA | MAP4215c | gi\|41410313 | 54 kDa | Metabolic Process | Y | |
| hypothetical protein | MAP4237c | gi\|41410335 | 29 kDa | Metabolic Process | | Y |
| Co-chaperonin GroES | MAP4264 | gi\|41410362 | 11 kDa | Response to Stimulus | | Y |
| fructose-1,6-bisphosphate aldolase | MAP4308c | gi\|41410406 | 34 kDa | carbohydrate metabolic process | | Y |
| TrxC; thioredoxin 1 | MAP4340 | gi\|41410438 | 12 kDa | Regulation of biological process | | Y |

TABLE 3

Matched ELISA and MAP fecal culture values for serum samples.

| | Sample Name | Serum IDEXX ELISA (S/P ratio) | MAP Fecal culture (CFU/tube) |
|---|---|---|---|
| p-ELISA/ high fecal | 17-58 | 1.579 | 200 |
| | 08-01 | 5.347 | 200 |
| | 23-25 | 1.968 | 200 |
| | 09-21 | 1.234 | 200 |
| | 15-78 | 1.305 | 200 |
| | 29-44 | 3.627 | 77 |
| | 23-144 | 1.034 | 200 |
| | 04-96 | 3.235 | 200 |
| | 04-137 | 2.172 | 200 |
| | 04-162 | 3.893 | 200 |
| | 08-41 | 2.153 | 200 |
| | 09-25 | 2.597 | 200 |
| p-ELISA/ low fecal | 08-08 | 1.720 | 1 |
| | 24-02 | 1.721 | 0 |
| | 09-14 | 2.608 | 4 |
| | 10-11 | 2.997 | 3 |
| | 17-105 | 4.289 | 7 |
| | 04-146 | 3.388 | 7 |
| n-ELISA/ high fecal | 32-118 | 0.313 | 200 |
| | 10-14 | 0.327 | 50 |
| | 04-155 | 0.636 | 200 |
| n-ELISA/ low fecal | 14-69 | 0.317 | 0 |
| | 32-97 | 0.296 | 0 |
| | 17-12 | 0.291 | 0 |
| | 23-96 | 0.289 | 0 |

Example 2: Recombinant Expression of MAP Antigen Proteins

MAP proteins (MAP0196c, MAP1569, MAP0471, MAP1981c, MAP3634, MAP1693c) were recombinantly expressed in *E. coli* strain BL21-CodonPlus(DE3)-RIPL.

MAP K10 nucleotide sequences obtained from the KEGG *Paratuberculosis* Genome reference bank were codon optimized for *E. coli* K12 using the Codon Optimization Tool (Integrated DNA Technologies). Gene sequences were synthesized as gBlocks (IDT), cloned into pET30a in-frame with a C-terminal 6×Histidine-tag using the isothermal assembly method, transformed into *E. coli* HB101, and plasmids sequenced to, confirm gene/sequence identity. Recombinant protein expression from these plasmids was carried out in *E. coli* BL21-CodonPlus(DE3)-RIPL. Briefly, overnight cultures were subcultured 1:100 in 600 mL Luria-Bertani (LB) broth supplemented with 50 µg/mL of kanamycin and 35 µg/mL of chloramphenicol, and grown at 37° C. to OD600 0.6. Protein expression was induced using 0.1 mM IPTG, and cultures incubated for an additional 16-20 hours at 25° C. Recombinant proteins were purified by immobilized metal affinity chromatography. Briefly, cell pellets were lysed by sonication in native purification buffer [NPB; 500 mM NaCl, 50 mM sodium phosphate monobasic, pH 8.0], cell debris removed by centrifugation, and 6× Histidine-tagged protein captured over a nickel-NTA resin. The resin was washed extensively with NPB-150 mM imidazole and 6×Histidine-tagged proteins eluted from the resin with NPB-400 mM imidazole. Eluted proteins were concentrated and dialyzed in PBS, pH 7.4 using Amicon Centrifugal filter units.

Figure 8:
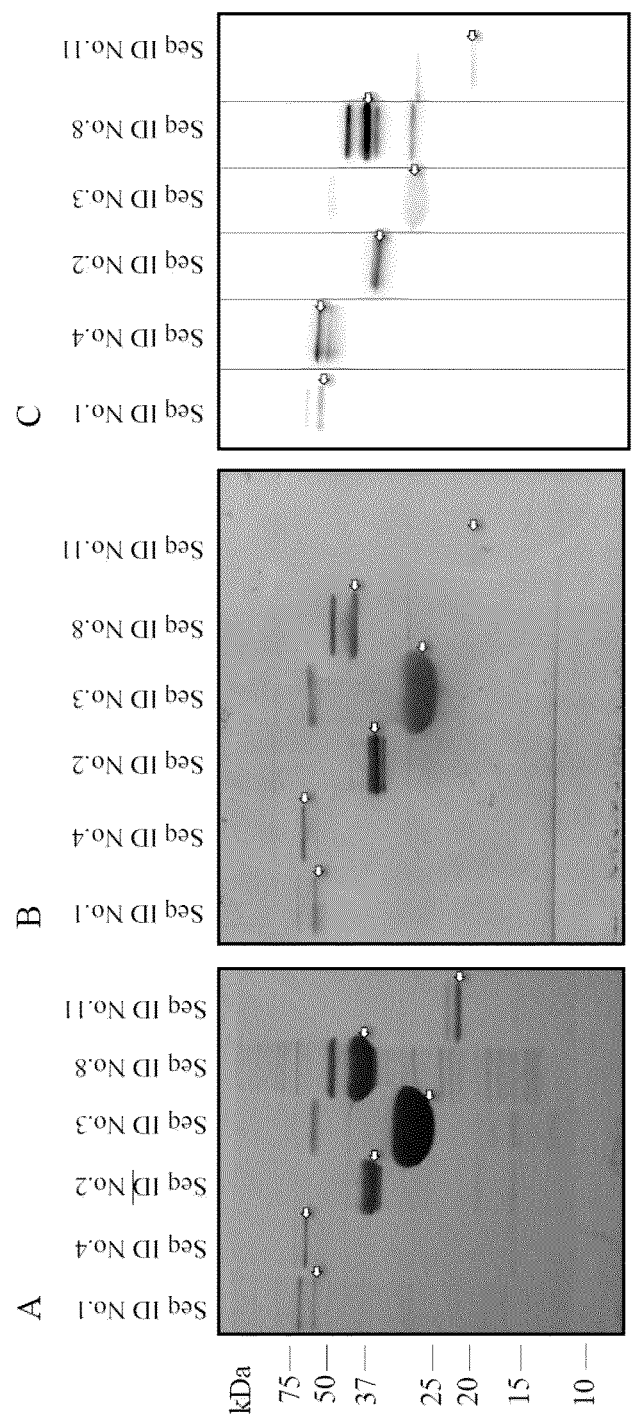
FIG. 8A shows SDS-PAGE of recombinant 6× histidine-tagged fusion proteins.
FIG. 8B shows an immunoblot of recombinant proteins reacted with His-Probe.
FIG. 8C shows an immunoblot of recombinant proteins reacted with respective anti-recombinant serum. Arrows denote the recombinant protein of study. Molecular mass standards are listed.

As shown in FIGS. 8A and 8B, SDS-PAGE of the recombinant 6× histidine-tagged fusion proteins showed bands at the expected molecular weights for each of MAP0196c (SEQ ID NO: 1), MAP1569 (SEQ ID NO: 4), MAP0471 (SEQ ID NO: 2), MAP1981c (SEQ ID NO: 3), MAP3634 (SEQ ID NO: 8) and MAP1693c (SEQ ID NO: 11).

*E. coli* culture supernatants from the recombinant protein expression experiments were also assessed by SDS-PAGE to determine if the recombinant proteins were secreted. The culture supernatant was prepared by removal of cells by centrifugation and filtration through a 0.22 µm PES membrane, and concentrating/dialyzing into PBS, pH 7.4 using Amicon Centrifugal filter units. Ten pg of total protein was resolved in a 12% w/v polyacrylamide gel, and stained with colloidal coomassie. MAP gene sequences were subcloned from the pET30a constructs (detailed above) into the pST-KT shuttle vector, and electroporated into *M. smegmatis* MC2155. *M. smegmatis* was cultured in 7H9 medium supplemented with 0.2% w/v glycerol, 0.02% w/v dextrose, 0.05% v/v Tween-80, and 20 µg/mL kanamycin at 37° C. for 40 h. Recombinant protein expression was induced using 50 ng/mL of anhydrotetracycline, and bacterial cells cultured for an additional 26 h. The culture supernatant was prepared and analyzed as described for *E. coli* above.

Figure 9:
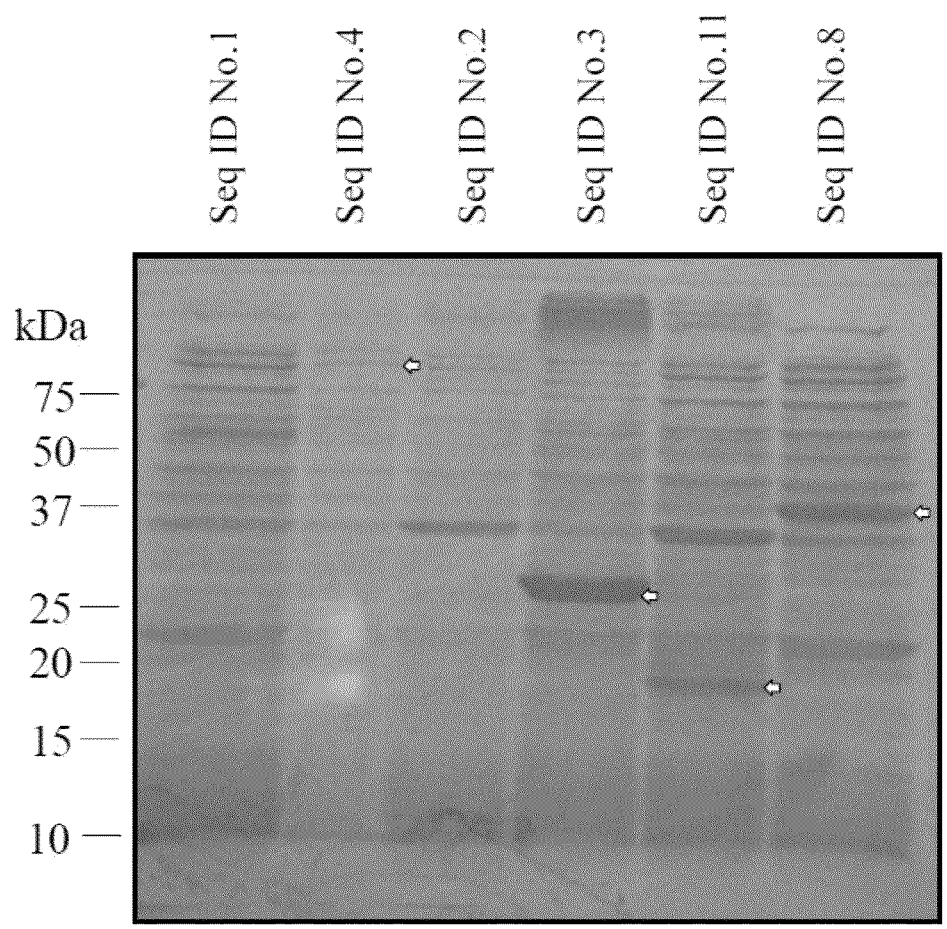
FIG. 9 shows SDS-PAGE of the culture supernatant of induced E. coli BL21-CodonPlus(DE3)-RIPL cells. Arrows denote the recombinant protein of study. Molecular mass standards are listed.
Figure 10:
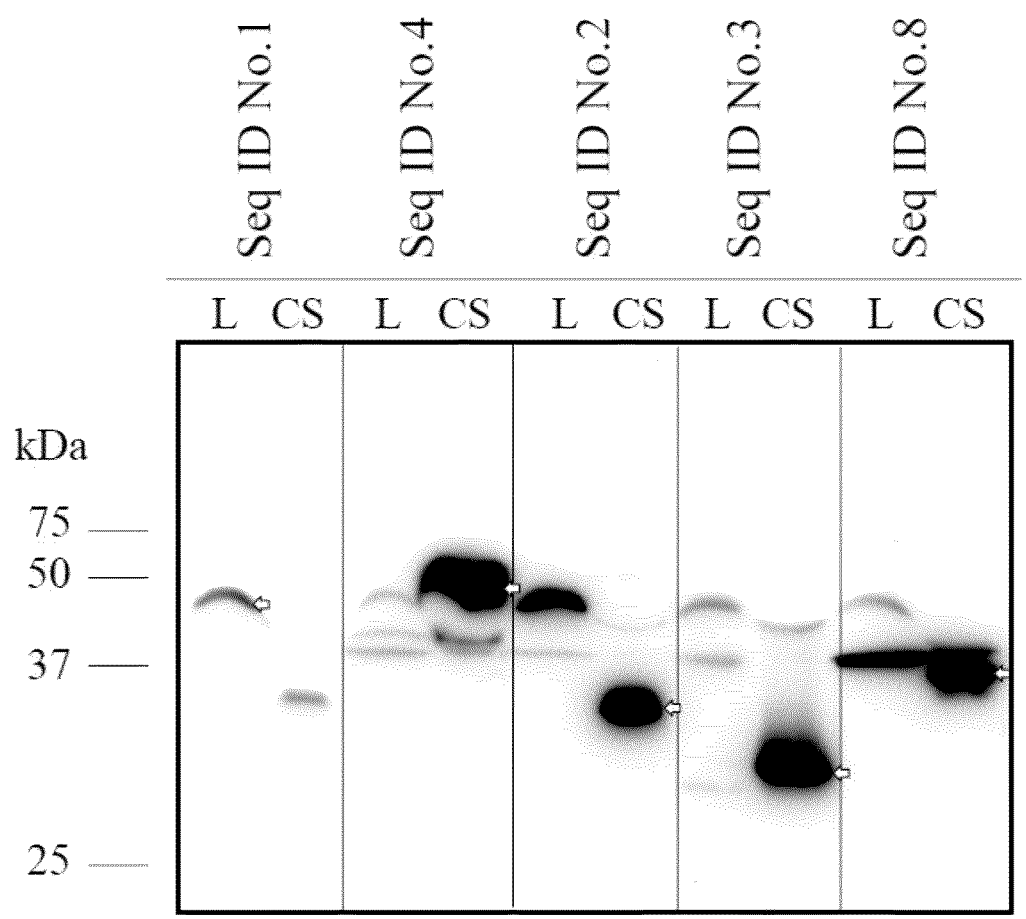
FIG. 10 shows an immunoblot of whole-cell lysates (L) and culture supernatants (CS) of M. smegmatis induced cultures. Arrows denote the recombinant protein of study. Molecular mass standards are listed.

As shown in FIGS. 9 and 10, four of the six MAP recombinant proteins were observed to be secreted in *E. coli* BL21-CodonPlus(DE3)-RIPL (MAP1569, MAP1981c, MAP1693c, MAP3634), and four of the six MAP recombinant proteins were observed to be secreted in *M. smegmatis* MC2155 (MAP1569, MAP0471, MAP1981c, MAP3634). Bioinformatic analyses failed in predicting and identifying a canonical secretory signal for export, suggesting that non-canonical sequences may direct secretion of these proteins.

Example 3: Immunogenicity of MAP Recombinant Proteins and Generation of Antibodies Sprague-Dawley rats were immunized with MAP recombinant proteins generated and polyclonal antiserum was generated for all proteins. Each MAP recombinant protein was observed to be immunogenic in rats.

A 1:1 emulsion of 50 µg of recombinant protein in PBS, pH 7.2 and TitreMax gold adjuvant was injected intramuscularly into a Sprague-Dawley rat. Recombinant MAP proteins were generated as set out in Example 2. Four subsequent immunizations consisting of 25 µg of protein emulsified in Freund's incomplete adjuvant were administered biweekly. Four days following the last immunization rats were euthanized and whole blood collected for serum preparation. The immunization protocols, use and care of all animals in this study were approved by the University of Guelph Animal Care and Use Committee. Immunoblotting was carried out as follows: one µg of each recombinant protein was resolved by SDS-PAGE, transferred to a nitrocellulose membrane, incubated with PBS-4% milk, and subsequently incubated overnight at 15° C. with rat polyclonal anti-recombinant serum diluted 1:1000 in PBS-1% milk. Blots were washed 3 times for 10 minutes with PBS-0.05% v/v Tween-20, and subsequently incubated with horseradish peroxidase conjugated anti-rat IgG diluted 1:7500 in PBS-1% milk for 1.5 h. After 3 washes with PBS-0.05% v/v Tween-20, immunocomplexes were reacted with a homemade ECL reagent (100 mM Tris-HCl, pH 8.8, 2 mM 4IPBA, 1.25 mM luminol, and 0.05% v/v $H_2O_2$) and detected using a chemiluminescent system.

Rat polyclonal antiserum was reacted against the recombinant protein to which it was immunized in addition to the other recombinant proteins to determine specificity. As shown in FIG. 8C, each polyclonal antiserum reacted exclusively with the immunizing recombinant protein, and not with the other recombinant proteins demonstrating the specificity of the antibodies.

Figure 11:
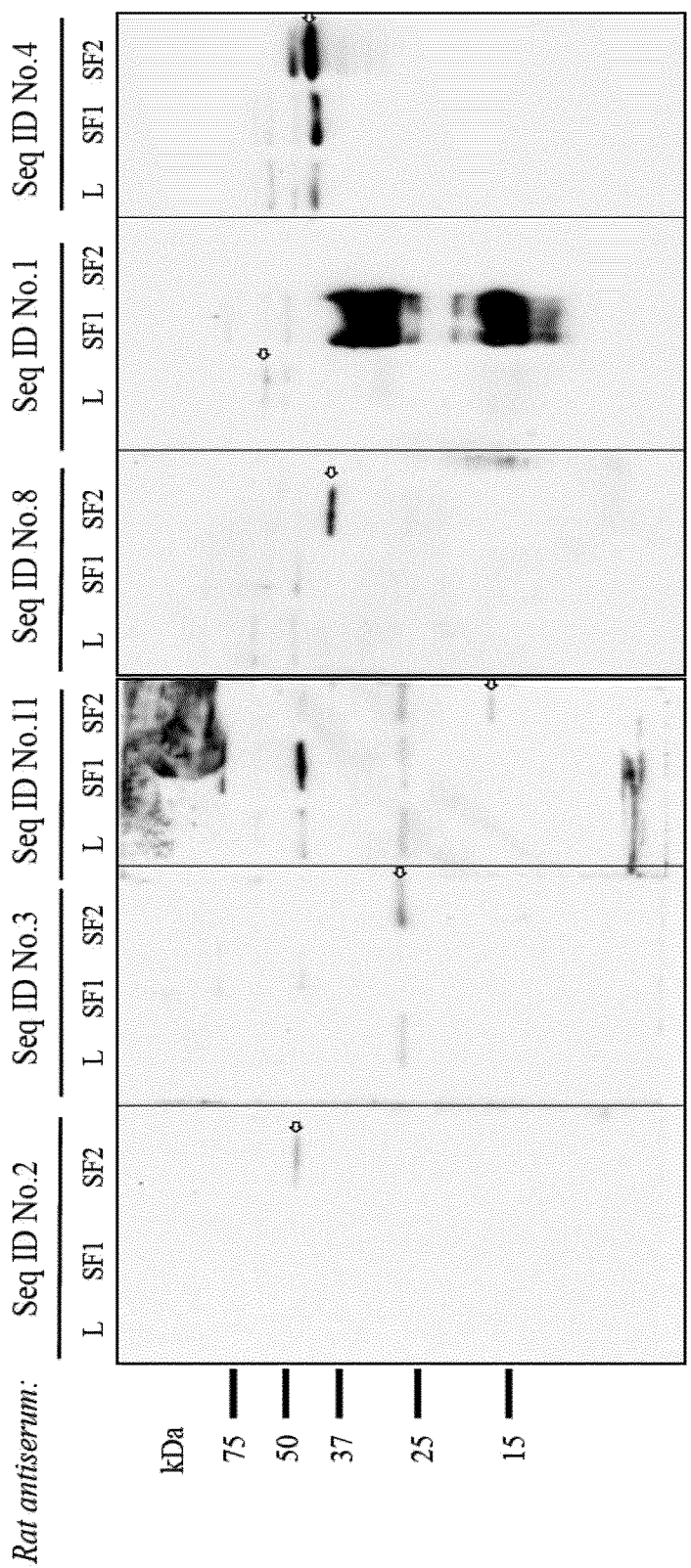
FIG. 11 shows an immunoblot of MAP whole-cell lysate (L) and culture supernatant (SF1 and SF2) with rat polyclonal anti-recombinant serum. Arrows denote expected molecular mass of native MAP protein. Molecular mass standards are listed.

The rat polyclonal anti-recombinant sera were also reacted against MAP whole-cell lysate and culture supernatant protein preparations as shown in FIG. 11. Ten µg of MAP whole-cell lysate and culture supernatant protein preparations were resolved by SDS-PAGE, transferred to a nitrocellulose membrane, and immunoblotting carried out as set out above.

The rat polyclonal antibodies detected native MAP secreted proteins with minimal cross-reactivity to other MAP proteins. As the polyclonal antibodies reacted with both the recombinant proteins and the native MAP antigens, and in light of the recombinant protein being used to generate this antiserum, the recombinant proteins appear to have retained epitopes similar to those of the MAP native protein, and the generated antibodies are antigen-specific.

Example 4: Specificity of Rat Polyclonal MAP Antibodies

Two complimentary approaches were used to show that the rat polyclonal antibodies are specific to the recognition of MAP protein epitopes.

Antiserum was cross-reacted with *M. avium* subsp. *hominissuis* whole-cell lysate and culture supernatant proteins (MAH; 98% nucleotide sequence similarity to MAP). Ten µg of MAH whole-cell lysate and culture supernatant protein preparations were resolved by SDS-PAGE, transferred to a nitrocellulose membrane, and immunoblotting was carried out as described above. For antiserum absorption, nitrocellulose squares were saturated with MAH lysate, blocked with PBS-4% milk, and incubated overnight with antiserum diluted 1:10 in PBS. The absorbed antiserum was diluted 1:1000 for use in immunoblots as described above.

Figure 12:
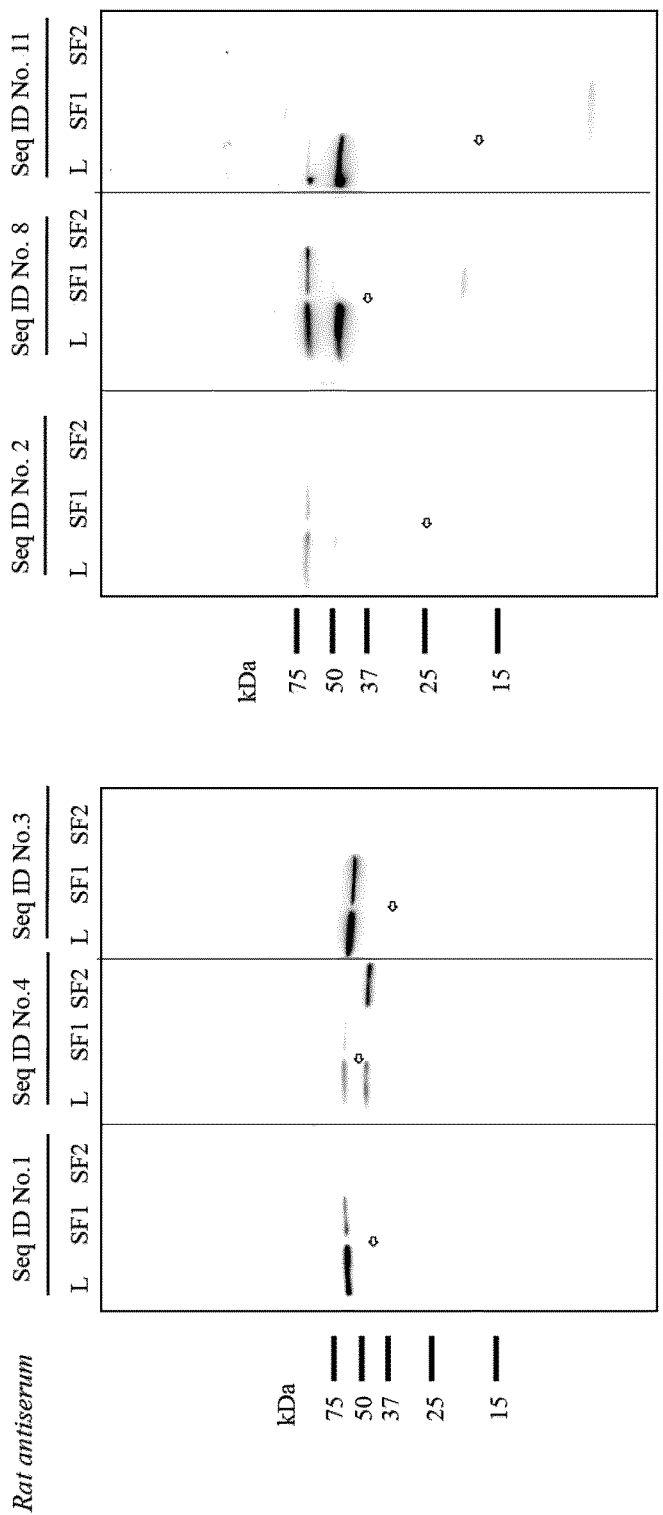
FIG. 12 shows an immunoblot of MAH whole-cell lysate (L) and culture supernatant (SF1 and SF2) with rat polyclonal anti-recombinant serum. Arrows denote expected molecular mass of homologous MAH proteins. Molecular mass standards are listed.

First, as shown in FIG. 12 anti-recombinant serum cross-reactivity was observed with only two MAH proteins unrelated in molecular mass to any of the recombinant proteins being tested.

Figure 13:
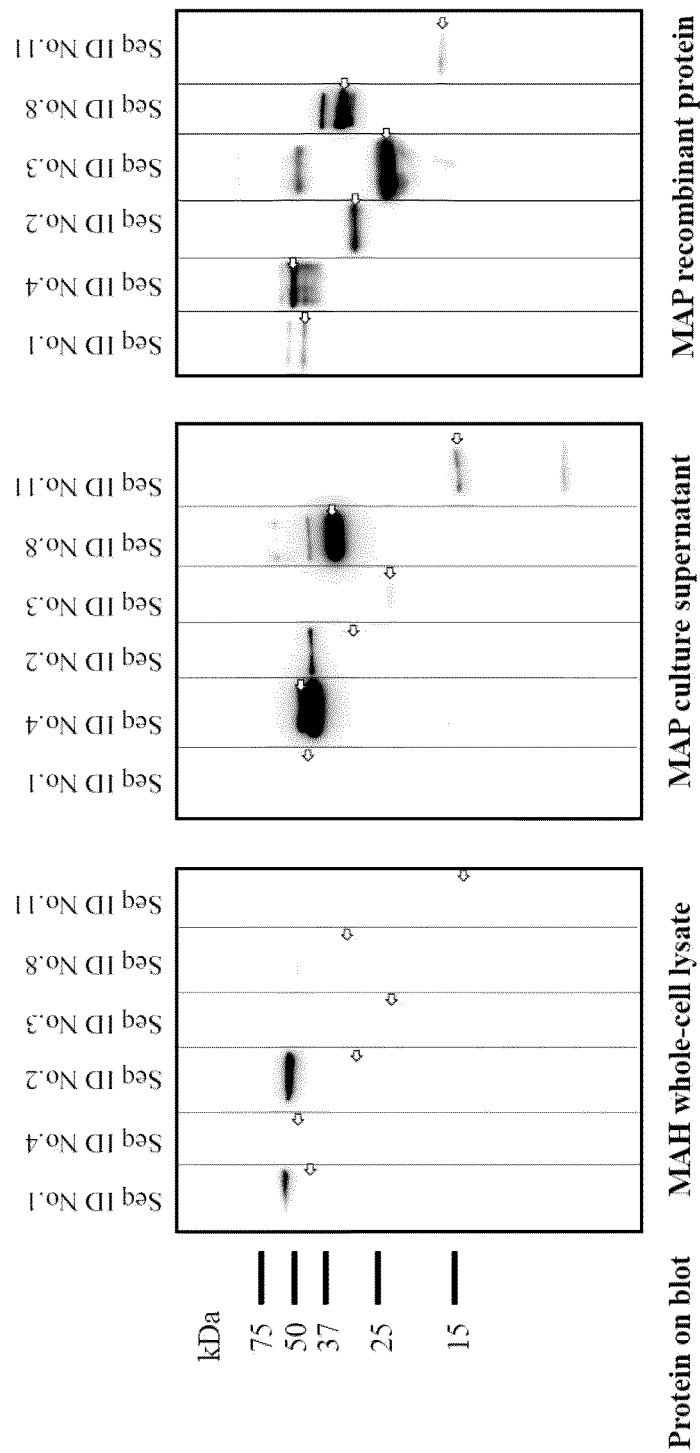
FIG. 13 shows an immunoblot of absorbed polyclonal rat anti-recombinant serum reacted against MAH whole-cell lysate, MAP culture supernatant, and MAP recombinant protein. Arrows denote expected molecular mass of recombinant protein of study. Molecular mass standards are listed.

Second, each antiserum was absorbed with MAH whole-cell lysate to remove antibodies recognizing epitopes in both MAH and MAP. For 3 of the 6 anti-recombinant absorbed serum antibodies to native MAP protein (anti-1981, anti-MAP3634, anti-1693c) were then detected. For all anti-recombinant absorbed serum antibodies were detected for the recombinant proteins (FIG. 13). Collectively, these data show that these proteins contain MAP-specific epitopes.

Example 5: Reactivity of MAP Recombinant Proteins with Sera from MAP Infected Cows MAP recombinant proteins (MAP1569, MAP0471, MAP3634, MAP1693) were reacted with sera from: MAP-fecal culture positive cows, MAP fecal culture negative cows, and 2-6 month old calves born to MAP-fecal culture negative dams and maintained in animal isolation units.

One µg of each recombinant protein was resolved by SDS-PAGE, transferred to a nitrocellulose membrane, blocked in PBS-4% milk, and incubated overnight at 15° C. with bovine serum diluted 1:100 in PBS-1% milk. Blots were washed 3 times for 10 minutes with PBS-0.05% v/v Tween-20, and incubated for 2 h with horseradish peroxidase conjugated anti-bovine IgG diluted 1:3000 in PBS-1% milk. After 3 washes with PBS-0.05% v/v Tween-20, immunocomplexes were reacted with a homemade ECL reagent (100 mM Tris-HCl, pH 8.8, 2 mM 4IPBA, 1.25 mM luminol, and 0.05% v/v $H_2O_2$) and detected using a chemiluminescent system.

Figure 14:
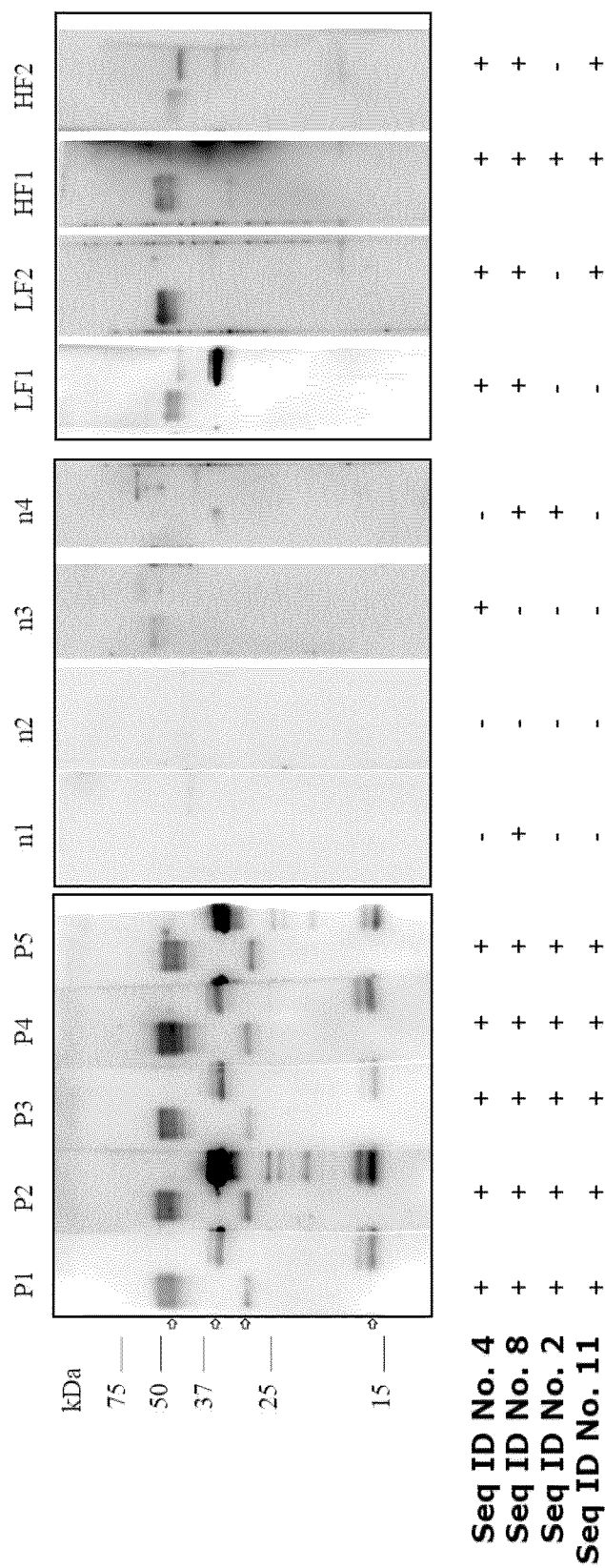
FIG. 14 shows an immunoblot of recombinant proteins MAP1569 (SEQ ID NO: 4), MAP0471 (SEQ ID NO: 2), MAP3634 (SEQ ID NO. 8), and MAP 1693c (SEQ ID NO. 11) with bovine sera. P1-P5; serum from ELISA and MAP fecal-culture positive cows, n1-n4; serum from cows on JD-positive herds that are both ELISA and MAP fecal-culture negative, nc1-nc7; serum from calves aged 2-6 months housed in animal isolation units. LF1-LF2; serum from low MAP fecal shedders (<10 CFU) and ELISA test positive, HF1-HF2; serum from high MAP fecal shedders (>50 CFU) and ELISA test negative. Arrows denote expected molecular mass of recombinant protein of study. Molecular mass standards are listed.
Figure 14:
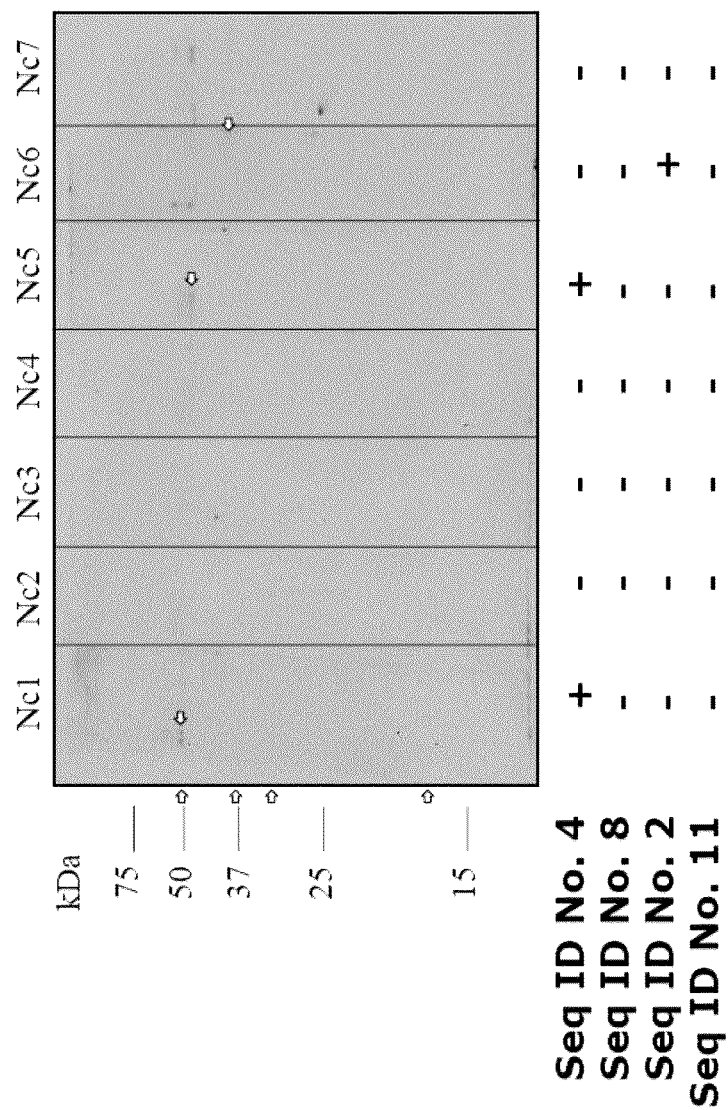

As shown in FIG. 14, antibodies to these four MAP recombinant proteins were detected in sera from MAP fecal-culture positive cows (n=5), but were absent in serum from MAP-negative calves (n=7). Two of the four serum samples from ELISA and MAP fecal-culture negative cows weakly reacted with one or more of the recombinant proteins. As these cows are in herds with known MAP fecal shedders, it is possible that these cows may: (i) have been exposed to the MAP bacterium, or (ii) are MAP-infected. Collectively, the results demonstrate that these recombinant proteins can differentiate MAP-infected from uninfected animals, as did the native MAP antigens initially discovered.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Tiwari A, VanLeeuwen J A, Dohoo I R, Keefe G P, Weersink A. 2008. Estimate of the direct production losses in Canadian dairy herds with subclinical *Mycobacterium avium* subspecies *paratuberculosis* infection. Can. Vet. J. 49:569-576.
2. USDA. 2008. Johne's disease on U. S. dairies. USDA APHIS VS National Animal Health Monitoring system, 1991-2007. No. 521.0408.
3. Harris N B, Barletta R G. 2001. *Mycobacterium avium* subsp. *paratuberculosis* in veterinary medicine. Clin. Microbiol. Rev. 14:489-512.
4. van Roermund H J, Bakker D, Willemsen P T, de Jong, M C. 2007. Horizontal transmission of *Mycobacterium avium* subsp. *paratuberculosis* in cattle in an experimental setting: Calves can transmit the infection to other calves. Vet. Microbiol. 122:270-279.
5. Collins M T, Eggleston V, Manning E J. 2010. Successful control of Johne's disease in nine dairy herds: Results of a six-year field trial. J. Dairy Sci. 93:1638-1643.
6. Wadhwa A, Hickling G J, Eda S. 2012. Opportunities for Improved Serodiagnosis of Human Tuberculosis, Bovine Tuberculosis, and *Paratuberculosis*. Vet. Med. Int. 2012: 674238. doi: 10.1155/2012/674238.
7. Collins M T, Gardner I A, Garry F B, Roussel A J, Wells S J. 2006. Consensus recommendations on diagnostic testing for the detection of *paratuberculosis* in cattle in the United States. J. Am. Vet. Med. Assoc. 229:1912-1919.
8. Sweeney R W, Whitlock R H, McAdams S, Fyock T. 2006. Longitudinal study of ELISA seroreactivity to *Mycobacterium avium* subsp. *paratuberculosis* in infected cattle and culture-negative herd mates. J. Vet. Diagn. Invest. 18:2-6.
9. Singh S V, Singh A V, Singh P K, Sohal J S, Singh N P. 2007. Evaluation of an indigenous ELISA for diagnosis of Johne's disease and its comparison with commercial kits. Indian. J. Microbiol. 47:251-258.
10. Clark Jr D L, Koziczkowski J J, Radcliff R P, Carlson R A, Ellingson J L. 2008. Detection of *Mycobacterium avium* subspecies *paratuberculosis*: Comparing fecal culture versus serum enzyme-linked immunosorbent assay and direct fecal polymerase chain reaction. J. Dairy Sci. 91:2620-2627.
11. Yokomizo Y, Yugi H, Merkal R S. 1985. A method for avoiding false-positive reactions in an enzyme-linked immunosorbent assay (ELISA) for the diagnosis of bovine *paratuberculosis*. Nihon. Juigaku. Zasshi. 47:111-119.
12. Samanich K M, Keen M A, Vissa V D, Harder J D, Spencer J S, Belisle J T, Zolla-Pazner S, Laal S. 2000. Serodiagnostic potential of culture filtrate antigens of *Mycobacterium tuberculosis*. Clin. Diagn. Lab. Immunol. 7:662-668.
13. Waters W R, Palmer M V, Thacker T C, Bannantine J P, Vordermeier H M, Hewinson R G, Greenwald R, Esfandiari J, McNair J, Pollock J M, Andersen P, Lyashchenko K P. 2006. Early antibody responses to experimental *Mycobacterium bovis* infection of cattle. Clin. Vaccine. Immunol. 13:648-654.
14. Cho D, Collins M T. 2006. Comparison of the proteosomes and antigenicities of secreted and cellular proteins produced by *Mycobacterium paratuberculosis*. Clin. Vaccine. Immunol. 13:1155-1161.
15. Shin S J, Cho D, Collins M T. 2008. Diagnosis of bovine *paratuberculosis* by a novel enzyme-linked immunosorbent assay based on early secreted antigens of *Mycobacterium avium* subsp. *paratuberculosis*. Clin. Vaccine. Immunol. 15:1277-1281.
16. Bannantine J P, Bayles D O, Waters W R, Palmer M V, Stabel J R, Paustian M L. 2008. Early antibody response against *Mycobacterium avium* subspecies *paratuberculosis* antigens in subclinical cattle. Proteome Sci. 6:5, doi: 10.1186/1477-5956-6-5.
17. Merkal R, Curran B. 1974. Growth and metabolic characteristics of *Mycobacterium paratuberculosis*. Appl. Microbiol. 28:276-279.
18. Blum H, Beier H, Gross H J. 1987. Improved silver staining of plant proteins, RNA and DNA in polyacrylamide gels. Electrophoresis. 8:93-99.

19. Woodward M P, Young Jr W W, Bloodgood R A. 1985. Detection of monoclonal antibodies specific for carbohydrate epitopes using periodate oxidation. J. Immunol. Methods. 78:143-153.
20. Nadkarini V, Lindhardt R. 1997. Enhancement of diaminobenzidine colorimetric signal in immunoblotting. BioTechniques. 23:385-388.
21. Mattow J, Schaible U E, Schmidt F, Hagens K, Siejak F, Brestrich G, Haeselbarth G, Müller E C, Jungblut P R, Kaufmann S H. 2003. Comparative proteome analysis of culture supernatant proteins from virulent *Mycobacterium tuberculosis* H37Rv and attenuated *M. bovis* BCG Copenhagen. Electrophoresis. 24:3405-3420.
22. Santema W, Overdijk M, Barends J, Krijgsveld J, Rutten V, Koets A. 2009. Searching for proteins of *Mycobacterium avium* subspecies *paratuberculosis* with diagnostic potential by comparative qualitative proteomic analysis of *mycobacterial* tuberculins. Vet. Microbiol. 138:191-196.
23. Cho D, Sung N, Collins M T. 2006. Identification of proteins of potential diagnostic value for bovine *paratuberculosis*. Proteomics. 6:5785-5794.
24. Leroy B, Roupie V, Noel-Georis I, Rosseels V, Walravens K, Govaerts M, Huygen K, Wattiez R. 2007. Antigen discovery: a postgenomic approach to *paratuberculosis* diagnosis. Proteomics. 7:1164-1176.
25. He Z, De Buck J. 2010. Localization of proteins in the cell wall of *Mycobacterium avium* subsp. *paratuberculosis* K10 by proteomic analysis. Proteome Sci. 8:21. doi: 10.1186/1477-5956-8-21.
26. Gomez M, Johnson S, Gennaro M L. 2000. Identification of Secreted Proteins of *Mycobacterium tuberculosis* by a Bioinformatic Approach. Infect. Immun. 68:2323-2327.
27. Målen H, Berven F S, Fladmark K E, Wiker H G. 2007. Comprehensive analysis of exported proteins from *Mycobacterium tuberculosis* H37Rv. Proteomics. 7:1702-1718.
28. DiGiuseppe Champion P A, Cox J S. 2007. Protein secretion systems in *Mycobacteria*. Cell. Microbiol. 9:1376-1384.
29. Daleke M H, Ummels R, Bawono P, Heringa J, Vandenbroucke-Grauls C M, Luirink J, Bitter W. 2012. General secretion signal for the *mycobacterial* type VII secretion pathway. Proc. Natl. Acad. Sci. USA. 109:11342-11347.
30. Jeffery C J. 1999. Moonlighting proteins. Trends. Biochem. Sci. 24:8-11.
31. Henderson B, Martin A. 2011. Bacterial virulence in the moonlighting: multitasking bacterial moonlighting proteins are virulence determinants in infectious disease. Infect. Immun. 79:3476-3491.
32. Tunio S A, Oldfield N J, Berry A, Ala'Aldeen D A, Wooldridge K G, Turner D P. 2010. The moonlighting protein fructose-1, 6-bisphosphate aldolase of *Neisseria meningitidis*: surface localization and role in host cell adhesion. Mol. Microbiol. 76:605-615.
33. Cehovin A, Coates A R, Hu Y, Riffo-Vasquez Y, Tormay P, Botanch C, Altare F, Henderson B. 2010. Comparison of the moonlighting actions of the two highly homologous chaperonin 60 proteins of *Mycobacterium tuberculosis*. Infect. Immun. 78:3196-3206.
34. Raghavan S, Manzanillo P, Chan K, Dovey C, Cox J S. 2008. Secreted transcription factor controls *Mycobacterium tuberculosis* virulence. Nature. 454:717-721.
35. Radosevich T J, Reinhardt T A, Lippolis J D, Bannantine J P, Stabel J R. 2007. Proteome and differential expression analysis of membrane and cytosolic proteins from *Mycobacterium avium* subsp. *paratuberculosis* strains K-10 and 187. J. Bacteriol. 189:1109-1117.
36. Weigoldt M, Meens J, Doll K, Fritsch I, Möbius P, Goethe R, Gerlach G F. 2011. Differential proteome analysis of *Mycobacterium avium* subsp. *paratuberculosis* grown in vitro and isolated from cases of clinical Johne's disease. Microbiology. 157:557-565.
37. Weigoldt M, Meens J, Bange F C, Pich A, Gerlach G F, Goethe R. 2013. Metabolic adaptation of *Mycobacterium avium* subsp. *paratuberculosis* to the gut environment. Microbiology. 159:380-391.
38. Xolalpa W, Vallecillo A J, Lara M, Mendoza-Hernandez G, Comini M, Spallek R, Singh M, Espitia C. 2007. Identification of novel bacterial plasminogen-binding proteins in the human pathogen *Mycobacterium tuberculosis*. Proteomics. 7:3332-3341.
39. Paustian M L, Kapur V, Bannantine J P. 2005. Comparative genomic hybridizations reveal genetic regions within the *Mycobacterium avium* complex that are divergent from *Mycobacterium avium* subsp. *paratuberculosis* isolates. J. Bacteriol. 187:2406-2415.

The invention claimed is:

1. A method of identifying a subject that has had an immunogenic response to *Mycobacterium avium* subspecies *paratuberculosis* (MAP) comprising:
providing a sample from the subject;
contacting the sample with a first protein to form a complex between the first protein and a first antibody;
contacting the sample with a second protein to form a complex between the second protein and a second antibody;
detecting the presence or absence of the complex between the first protein and the first antibody and detecting the complex between the second protein and the second antibody thereby determining the presence or absence of the first antibody and second antibody in the sample;
wherein the first antibody and second antibody selectively bind to different proteins selected from MAP3634 (SEQ ID NO: 8), MAP0471 (SEQ ID NO: 2), MAP0196c (SEQ ID NO: 1), MAP1981c (SEQ ID NO: 3), MAP0281 (SEQ ID NO: 5), MAP3428c (SEQ ID NO: 7), MAP2785 (SEQ ID NO: 9) and MAP2786c (SEQ ID NO: 10), in a sample from the subject, wherein the presence of the first antibody and the second antibody in the sample indicates that the subject has had an immunogenic response to MAP.

2. The method of claim 1, wherein the first antibody selectively binds to MAP3634 (SEQ ID NO: 8).

3. The method of claim 1, wherein the first antibody and second antibody selectively bind to different proteins selected from MAP0471 (SEQ ID NO: 2), MAP0196c (SEQ ID NO: 1), and MAP1981c (SEQ ID NO: 3).

4. The method of claim 2, wherein the first antibody and second antibody selectively bind to MAP3634 (SEQ ID NO: 8) and MAP0471 (SEQ ID NO: 2), wherein the presence of antibodies that selectively bind to MAP3634 and MAP0471 indicates that the subject has had an immunogenic response to MAP.

5. The method of claim 1, further comprising contacting the sample with a third protein to from a complex between the third protein and a third antibody, wherein the first antibody, second antibody and third antibody selectively bind to different proteins selected from MAP3634 (SEQ ID NO: 8), MAP0471 (SEQ ID NO: 2), MAP0196c (SEQ ID NO: 1), MAP1981c (SEQ ID NO: 3), MAP0281 (SEQ ID NO: 5), MAP3428c (SEQ ID NO: 7), MAP2785 (SEQ ID NO: 9) and MAP2786c (SEQ ID NO: 10).

6. The method of claim 5, wherein the first antibody, second antibody and third antibody selectively bind to different proteins selected from MAP3634 (SEQ ID NO: 8), MAP0471 (SEQ ID NO: 2) and MAP1693c (SEQ ID NO: 11), wherein the presence of antibodies that selectively bind to MAP3634, MAP0471 and MAP1693c indicates that the subject has had an immunogenic response to MAP.

7. The method of claim 5, further comprising contacting the sample with a fourth protein to from a complex between the fourth protein and a fourth antibody, wherein the first antibody, second antibody, third antibody and fourth antibody selectively bind to different proteins selected from MAP3634 (SEQ ID NO: 8), MAP0471 (SEQ ID NO: 2), MAP0196c (SEQ ID NO: 1), MAP1981c (SEQ ID NO: 3), MAP0281 (SEQ ID NO: 5), MAP3428c (SEQ ID NO: 7), MAP2785 (SEQ ID NO: 9) and MAP2786c (SEQ ID NO: 10).

8. The method of claim 1, wherein the subject is pre-symptomatic for Johne's disease.

9. The method of claim 1, wherein the sample comprises blood, feces, milk, colostrum, urine, tissue or semen.

10. The method of claim 1, wherein the sample comprises serum.

11. The method of claim 1, wherein the subject is a ruminant.

12. The method of claim 1, wherein detecting the presence or absence of the complex between the first protein and the first antibody or detecting the complex between the second protein and the second antibody comprises 1D or 20 immunoblotting.

13. The method of claim 1, wherein detecting the presence or absence of the complex between the first protein and the first antibody or detecting the complex between the second protein and the second antibody comprises an enzyme-linked immunosorbent assay (ELISA).

14. A method for maintaining a herd free from Johne's disease, the method comprising:
   providing a sample from a subject in the herd or prior to being introduced into the herd;
   contacting the sample with a first protein to form a complex between the first protein and a first antibody;
   contacting the sample with a second protein to form a complex between the second protein and a second antibody;
   detecting the presence or absence of the complex between the first protein and the first antibody and detecting the complex between the second protein and the second antibody in the sample, wherein the first antibody and second antibody selectively bind to different proteins selected from MAP3634 (SEQ ID NO: 8), MAP0471 (SEQ ID NO: 2), MAP0196c (SEQ ID NO: 1), MAP1981c (SEQ ID NO: 3), MAP0281 (SEQ ID NO: 5), MAP3428c (SEQ ID NO: 7), MAP2785 (SEQ ID NO: 9) and MAP2786c (SEQ ID NO: 10);
   removing or quarantining from the herd a subject having the presence of the complex between the first protein and the first antibody and the complex between the second protein and the second antibody in the sample.

15. The method of claim 14, wherein the sample comprises blood, feces, milk, colostrum, urine, tissue or semen.

16. The method of claim 14, wherein the sample comprises serum or milk.

17. The method of claim 14, wherein the herd is a herd of cattle.

18. The method of claim 14, wherein the first antibody and second antibody selectively bind to different proteins selected from MAP3634 (SEQ ID NO: 8), MAP0471 (SEQ ID NO: 2), MAP0196c (SEQ ID NO: 1), and MAP1981c (SEQ ID NO: 3).

19. The method of claim 14, wherein the first protein and second protein comprise an epitope within a protein selected from MAP3634 (SEQ ID NO: 8), MAP0471 (SEQ ID NO: 2), MAP0196c (SEQ ID NO: 1), MAP1981c (SEQ ID NO: 3), MAP0281 (SEQ ID NO: 5), MAP3428c (SEQ ID NO: 7), MAP2785 (SEQ ID NO: 9) and MAP2786c (SEQ ID NO: 10).

20. The method of claim 14, wherein detecting the presence or absence of the complex between the first protein and the first antibody or detecting the complex between the second protein and the second antibody comprises an enzyme-linked immunosorbent assay (ELISA).

* * * * *

UNITED STATES PATENT AND TRADEMARK OFFICE
CERTIFICATE OF CORRECTION

| | |
|---|---|
| PATENT NO. | : 9,879,057 B2 |
| APPLICATION NO. | : 15/024238 |
| DATED | : January 30, 2018 |
| INVENTOR(S) | : Lucy M. Mutharia and Antonio Facciuolo |

It is certified that error appears in the above-identified patent and that said Letters Patent is hereby corrected as shown below:

In Claim 12 at Column 53, Line 2, "20" should read --2D--.

Signed and Sealed this
Fifth Day of June, 2018

Andrei Iancu
*Director of the United States Patent and Trademark Office*

SEQUENCE LISTING

<160> NUMBER OF SEQ ID NOS: 11

<210> SEQ ID NO 1
<211> LENGTH: 450
<212> TYPE: PRT
<213> ORGANISM: Mycobacterium avium

<400> SEQUENCE: 1

Met Ser Gln Ala Pro Glu Lys Asp Leu Pro Glu Ala Gly Glu Ala Pro
1               5                   10                  15

Ala Val Glu Thr Thr Ala Ala Ser Ala Phe Leu Trp Pro Arg Ser Leu
            20                  25                  30

Gln Ala Arg Ala Thr Arg Arg Ala Leu Leu Leu Thr Ala Leu Gly Gly
        35                  40                  45

Leu Leu Ile Ala Gly Leu Val Thr Ala Leu Pro Val Gly Gly Thr Gly
    50                  55                  60

Ser Gly Arg Leu Leu Asp Ala Ser Pro Val Arg Ser Thr Gly Ala Lys
65                  70                  75                  80

Ser Asp Ala Ala Phe Asn Arg Ala Ala Ser Gly Glu Cys Leu Met Trp
                85                  90                  95

Pro Asp Thr Thr Pro Glu Ser Ala Lys Ile Val Asn Cys Gly Asp Asp
            100                 105                 110

His Lys Phe Glu Val Ala Glu Ser Ile Asp Met Arg Thr Phe Pro Gly
        115                 120                 125

Ser Glu Tyr Gly Pro Asn Ala Ala Pro Pro Thr Pro Ala Arg Ile Gln
    130                 135                 140

Gln Ile Thr Gln Glu Gln Cys Glu Ala Val Arg Asn Tyr Leu Gly
145                 150                 155                 160

Pro Lys Phe Asp Pro Asn Ser Lys Phe Thr Val Ser Leu Leu Trp Pro
                165                 170                 175

Gly Asp Arg Ala Trp Arg Gln Gly Asp Arg Arg Met Leu Cys Gly
            180                 185                 190

Leu Gln Leu Pro Gly Ala Asn Asn Gln Gln Gln Val Phe Lys Gly Lys
        195                 200                 205

Val Ala Asp Val Asp Gln Ser Lys Ile Trp Pro Ala Gly Thr Cys Leu
    210                 215                 220

Gly Ile Asp Ser Ala Thr Asn Gln Pro Thr Asp Val Pro Val Asp Cys
225                 230                 235                 240

Ala Ala Pro His Ala Met Glu Val Thr Gly Thr Val Asn Leu Ala Glu
                245                 250                 255

Lys Phe Pro Gly Ala Leu Pro Ala Glu Pro Asp Gln Asp Ala Phe Ile
            260                 265                 270

Lys Asp Ser Cys Thr Lys Met Thr Asp Ala Tyr Leu Ala Pro Val Lys
        275                 280                 285

Leu Arg Thr Thr Thr Leu Thr Leu Ile Tyr Pro Thr Val Pro Leu Ala
    290                 295                 300

Ser Trp Thr Ala Gly Ser Arg Glu Val Ala Cys Ser Ile Gly Ala Thr
305                 310                 315                 320

Leu Gly Asn Gly Gly Trp Ala Thr Leu Leu Asn Ser Ala Lys Gly Gln
                325                 330                 335

Leu Leu Ile Asn Gly Gln Pro Val Pro Pro Asp Ile Pro Glu
            340                 345                 350

Glu Arg Leu Ser Met Pro Pro Ile Pro Leu Gln Ala Pro Ala Gln Ser
        355                 360                 365

Pro Ser Thr Gln Ser Gly Ser Ala Ala Pro Glu Met Pro Arg Asn
    370                 375                 380

Asn Gln His Leu Pro Gly Gln Gln Pro Val Val Thr Gln Pro Pro Gln
385                 390                 395                 400

Ala Pro Pro Pro Val Asp Asn Gly Ala Pro Pro Ala Asn Pro
                405                 410                 415

Ala Pro Glu Ala Pro Ala Pro Val Pro Pro Ala Ala Pro
            420                 425                 430

Pro Pro Pro Pro Ala Pro Glu Ala Pro Gly Gly Pro Pro Pro
        435                 440                 445

Ala Gly
    450

<210> SEQ ID NO 2
<211> LENGTH: 277
<212> TYPE: PRT
<213> ORGANISM: Mycobacterium avium

<400> SEQUENCE: 2

Met Thr Trp Ala Tyr Ala Ala Asn Val Leu Asp Leu Glu Pro Arg Gly
1               5                   10                  15

Pro Leu Pro Thr Glu Ile Tyr Trp Arg Arg Gly Leu Ala Val Gly
            20                  25                  30

Ile Ala Val Val Val Ile Gly Val Ala Ala Ala Val Ile Ala Phe
        35                  40                  45

Met Gly His Ser Ala Gly Ala Lys Pro Ala Asn Ala Asp Lys Pro Asn
    50                  55                  60

Ser Ala Gln Ser Lys Pro Gly Ser Pro Ala Pro Gln Ala Pro Ala Pro
65                  70                  75                  80

Pro Gly Pro Glu Gly Pro Ala Pro Ala Val Pro Pro Ala Gln Gly Gln
                85                  90                  95

Asn Pro Glu Thr Pro Thr Pro Thr Ala Ala Val Gln Pro Pro Val
            100                 105                 110

Leu Lys Glu Gly Asp Asp Cys Pro Asp Ser Thr Leu Ala Val Lys Gly
            115                 120                 125

Leu Thr Asn Ala Pro Gln Tyr Phe Ile Gly Asp Gln Pro Lys Phe Thr
            130                 135                 140

Met Val Val Thr Asn Ile Gly Leu Val Ala Cys Lys Arg Asp Val Gly
145                 150                 155                 160

Ala Ala Val Leu Ala Ala Tyr Val Tyr Ser Leu Asp Asn Lys Arg Leu
                165                 170                 175

Trp Ser Asn Leu Asp Cys Ala Pro Ser Asn Glu Thr Leu Ile Lys Thr
            180                 185                 190

Phe Thr Pro Gly Glu Gln Val Thr Thr Ala Val Thr Trp Thr Gly Met
        195                 200                 205

Gly Ser Ala Pro His Cys Pro Leu Pro Arg Pro Ala Ile Gly Pro Gly
    210                 215                 220

Thr Tyr Asn Leu Val Val Gln Leu Gly Asn Leu Arg Ser Gln Pro Val
225                 230                 235                 240

Pro Phe Ile Met Asn Gln Pro Pro Pro Pro Gly Pro Val Pro Gly
                245                 250                 255

Pro Gly Gln Pro Gly Ala Val Pro Gln Pro Glu Ala Pro Pro Val Pro
            260                 265                 270

Pro Pro Pro Ala Gly
        275

<210> SEQ ID NO 3
<211> LENGTH: 245
<212> TYPE: PRT
<213> ORGANISM: Mycobacterium avium

<400> SEQUENCE: 3

Met Lys Ala Asp Val Ala Gln Gln Arg Ser Leu Leu Glu Leu Ala Asn
1               5                   10                  15

Val Asp Ala Glu Leu Ser Arg Leu Ala His Arg Ala Glu His Leu Pro
            20                  25                  30

Glu Gln Gln Ala Cys Glu Arg Met Gln Gln Glu Tyr Asp Ala Ala Gly
        35                  40                  45

Asp Arg Leu Gly Ala Val Arg Ile Ala Leu Glu Asp Ile Asp Ala His
    50                  55                  60

Val Leu Arg Leu Glu Ala Glu Val Asp Ala Val Arg Gln Arg Glu Asp
65                  70                  75                  80

-continued

Arg Asp Arg Ser Leu Leu Gln Ser Gly Ala Ile Asp Ala Lys Gln Leu
                85                  90                  95

Ala Asp Leu Gln His Glu Leu Glu Thr Leu Gln Arg Arg Gln Thr Ser
            100                 105                 110

Leu Glu Asp Ser Leu Leu Glu Val Met Glu Arg Arg Glu Glu Leu Gln
        115                 120                 125

Ala Gln Leu Asp Gly Glu Gln Gln Ala Leu Lys Glu Leu Glu Ala Glu
    130                 135                 140

Met Ala Thr Ala Arg Arg Asp Leu Asp Ala Ala Arg Gly Glu Ile Ser
145                 150                 155                 160

Glu Ser Arg Ala Leu His Ser Ser Arg Arg Asp Ala Leu Ser Ala Glu
                165                 170                 175

Leu Asp Pro Glu Leu Phe Ala Leu Tyr Glu Arg Gln Arg Ala Arg Gly
            180                 185                 190

Gly Pro Gly Ala Gly Gln Leu Leu Gly Arg Arg Cys Gly Ala Cys Arg
        195                 200                 205

Leu Glu Ile Asp Arg Gly Glu Leu Ser Arg Ile Ser Ala Ala Ala Glu
    210                 215                 220

Asp Asp Val Val Arg Cys Pro Glu Cys Gly Ala Ile Leu Leu Arg Val
225                 230                 235                 240

Lys Gly Ser Gly Gln
                245

<210> SEQ ID NO 4
<211> LENGTH: 368
<212> TYPE: PRT
<213> ORGANISM: Mycobacterium avium

<400> SEQUENCE: 4

Met Asp Gln Val Glu Ala Thr Ser Thr Arg Arg Lys Gly Leu Trp Thr
1               5                   10                  15

Thr Leu Ala Ile Thr Thr Val Ser Gly Ala Ser Ala Val Ala Ile Ala
            20                  25                  30

Leu Pro Ala Thr Ser His Ala Asp Pro Glu Val Pro Thr Pro Val Pro
        35                  40                  45

Pro Ser Thr Ala Thr Ala Pro Pro Ala Pro Ala Pro Asn Gly Gln
    50                  55                  60

Pro Ala Pro Asn Ala Gln Pro Ala Pro Gly Ala Pro Ala Pro Asn Gly
65                  70                  75                  80

Gln Pro Ala Pro Ala Ala Pro Pro Asn Asp Pro Asn Ala Ala Pro
                85                  90                  95

Pro Pro Val Gly Ala Pro Pro Asn Gly Ala Pro Pro Pro Val Asp
            100                 105                 110

Pro Asn Ala Pro Pro Pro Pro Ala Asp Pro Asn Ala Gly Arg Ile
        115                 120                 125

Pro Asn Ala Val Gly Gly Phe Ser Tyr Val Leu Pro Ala Gly Trp Val
    130                 135                 140

Glu Ser Asp Ala Ser His Leu Asp Tyr Gly Ser Ala Leu Leu Ser Lys
145                 150                 155                 160

Val Thr Gly Pro Pro Pro Met Pro Asp Gln Pro Pro Val Ala Asn
                165                 170                 175

Asp Thr Arg Ile Val Met Gly Arg Leu Asp Gln Lys Leu Tyr Ala Ser
            180                 185                 190

Ala Glu Ala Asn Asn Ala Lys Ala Ala Val Arg Leu Gly Ser Asp Met
        195                 200                 205

Gly Glu Phe Phe Met Pro Tyr Pro Gly Thr Arg Ile Asn Gln Asp Ser
    210                 215                 220

Thr Pro Leu Asn Gly Ala Asn Gly Ser Thr Gly Ser Ala Ser Tyr Tyr
225                 230                 235                 240

Glu Val Lys Phe Ser Asp Ala Ser Lys Pro Asn Gly Gln Ile Trp Thr
                245                 250                 255

Gly Val Ile Gly Ser Ala Asn Gly Gly Asn Ala Gln Arg Trp Phe Val
            260                 265                 270

Val Trp Leu Gly Thr Ser Asn Asp Pro Val Asp Lys Val Ala Ala Lys
        275                 280                 285

Ala Leu Ala Glu Ser Ile Gln Ala Trp Thr Pro Ala Ala Pro Pro
    290                 295                 300

Ala Ala Pro Gly Gly Pro Gly Ala Pro Ala Pro Gly Ala Pro Gly Thr
305                 310                 315                 320

Pro Ala Ala Pro Gly Ala Pro Ala Ala Pro Ala Pro Ala Ala Pro Gly
                325                 330                 335

Ala Pro Ala Ala Pro Gly Ala Pro Ala Pro Gly Gln Ala Pro Ala Val
            340                 345                 350

Glu Val Ser Pro Thr Pro Thr Pro Thr Pro Gln Gln Thr Leu Ser Ala
        355                 360                 365

<210> SEQ ID NO 5
<211> LENGTH: 157
<212> TYPE: PRT
<213> ORGANISM: Mycobacterium avium

<400> SEQUENCE: 5

Met Thr Arg Lys Ala Glu Ile Val Ala Val Phe Ala Ile Cys Thr Ala
1               5                   10                  15

Phe Met Thr Ala Ser Gly Ala Phe Gly Gly Phe Ala Ala Arg Ala Asp
                20                  25                  30

Asp Pro Glu Ile Leu Tyr Asn Gly Ile Asn Gln Leu Arg Gln Ala Cys
            35                  40                  45

Gly Pro Ile Ala Glu Asp Pro Arg Leu Thr Glu Ala Ala Gln Gln His
    50                  55                  60

Ala Asp Asp Met Leu Arg Asn Gly Val Ser Gly His Ile Gly Ser Asp
65                  70                  75                  80

Gly Ser Ser Pro Gln Ala Arg Ile Ala Ala Ala Gly Tyr Arg Ser Arg
                85                  90                  95

Tyr Ser Gly Glu Ile Val Phe Trp Ala Thr Gly Ser Ala Ala Thr Pro
            100                 105                 110

Ser Glu Ala Leu Asp Met Trp Met Gln Ser Pro Pro His Arg Ala Ile
        115                 120                 125

Ile Leu Asn Cys Gly Phe Asn Ala Gly Phe Ala Thr Ala Arg Asp
    130                 135                 140

Gly Asn Lys Met Thr Ala Val Gly Asp Phe Ala Thr Ser
145                 150                 155

<210> SEQ ID NO 6
<211> LENGTH: 151
<212> TYPE: PRT
<213> ORGANISM: Mycobacterium avium

<400> SEQUENCE: 6

Met Ala Phe Ser His Ile Ala Ser Lys Thr Thr Ala Ala Thr Ala Ala
1               5                   10                  15

-continued

```
Leu Ala Ala Ala Gly Leu Leu Ala Ala Ala Pro Ala Phe Ala Asp Pro
            20                  25                  30

Gln Val Leu Gln Phe Gly Gln Met Ala Glu Ile Ser Ser Asn Gly Gly
        35                  40                  45

Thr Ile Asp Tyr Thr Val Ser Asn Leu Gln Pro Ser Gly His Asn Asp
    50                  55                  60

Gly Val Trp Tyr Ser Asp Val Thr Ala Lys Gly Val Ser Gly Asn Ala
65                  70                  75                  80

Val Pro Asn Ile Ala Asp Phe Asn Ala Arg Ala Val Asn Ser Ser Thr
                85                  90                  95

Phe Ala Val Met Lys Gly Asn Gln Thr Asp Gly Leu Pro Glu Gly Pro
            100                 105                 110

Leu Pro Leu Gly Thr Pro Val Thr Gly Arg Leu Tyr Phe Asp Val Arg
        115                 120                 125

Asn Gly Thr Asn Pro Asp Ser Val Val Tyr Arg Asp Ala Gly Gly Thr
    130                 135                 140

Asp Lys Val Val Trp Lys Ser
145                 150

<210> SEQ ID NO 7
<211> LENGTH: 235
<212> TYPE: PRT
<213> ORGANISM: Mycobacterium avium

<400> SEQUENCE: 7

Met Ser Gly Gly Cys Ala Arg Ile Trp Arg Met Asn Leu Arg Gly Trp
1               5                   10                  15

Pro Val Val Gly Pro Ala Ile Gly Thr Val Val Ala Val Ala Leu Ser
            20                  25                  30

Val Val Ala Ile Thr Cys Gly Pro Ala Pro Arg Ala Ala Ala Asp Gly
        35                  40                  45

Cys Pro Asp Val Gln Leu Ile Phe Ala Arg Gly Thr Ala Glu Pro Pro
    50                  55                  60

Gly Leu Gly Ala Val Gly Asp Ala Leu Phe Ala Ala Leu Gln Pro Ala
65                  70                  75                  80

Leu Gly Asn Arg Asn Val Asp Ala Tyr Ala Val Asn Tyr Pro Ala Ser
                85                  90                  95

Tyr Asn Phe Leu Thr Thr Ala Asp Gly Ala Asn Asp Ala Arg Asp His
            100                 105                 110

Ile Ala Glu Met Val Asp Arg Cys Pro Ser Thr Arg Leu Val Leu Gly
        115                 120                 125

Gly Phe Ser Gln Gly Ala Ala Ala Val Ser Met Leu Ala Gly Val Pro
    130                 135                 140

Pro Val Gly Gln Arg Ile Gly Asn Phe Gly Ser Ala Pro Pro Leu Asp
145                 150                 155                 160

Pro Gly Leu Ala Ser Lys Ile Ala Ala Val Ala Val Phe Gly Asn Pro
                165                 170                 175

Gly Asn Arg Phe Asn Thr Pro Leu Ser Thr Thr Gly Ala Phe Ala Gly
            180                 185                 190

Arg Ala Ile Asp Leu Cys Ser Asp Gly Asp Pro Val Cys Val Val Gly
        195                 200                 205

Gly Arg Asp Arg Asp Ala His His Val Tyr Glu Asp Pro Pro Tyr Pro
    210                 215                 220

Ala Gln Ala Ala Gly Phe Ile Ala Gly Arg Val
```

```
225                 230                 235

<210> SEQ ID NO 8
<211> LENGTH: 345
<212> TYPE: PRT
<213> ORGANISM: Mycobacterium avium

<400> SEQUENCE: 8

Met Ser Gly Gly Met Pro Met Ser Gly Trp Thr Arg Gly Thr Leu Phe
1               5                   10                  15

Ala Ala Leu Asn Ala Ala Val Val Ser Val Val Gly Leu Ala Leu Val
                20                  25                  30

Leu Ser Ala Gly Pro Ala Leu Ala Asp Pro Asp Pro Ala Pro Ala Asp
            35                  40                  45

Pro Gly Ala Val Ala Ala Pro Gly Pro Pro Ala Pro Pro Asp Pro
        50                  55                  60

Leu Ala Pro Pro Pro Pro Asp Pro Leu Ala Pro Pro Pro Ala
65                  70                  75                  80

Ala Pro Pro Ala Pro Trp Leu Pro Pro Ala Ala Gln Pro Ala Ala Ala
                85                  90                  95

Pro Ala Ala Gly Gln Asp Pro Thr Pro Phe Thr Gly Thr Pro Pro Phe
            100                 105                 110

Gly Pro Pro Thr Phe Val Pro Lys Thr Gly Ser Thr Val Gly Val Ala
        115                 120                 125

Gln Pro Ile Ile Ile Asn Phe Pro Gly Arg Val Asp Asp Ala Gly Ala
130                 135                 140

Ala Ile Ser Ala Val His Val Ser Ser Val Pro Val Pro Gly Lys
145                 150                 155                 160

Phe Tyr Trp Met Thr Pro Thr Gln Leu Arg Trp Arg Pro Leu Ser Phe
                165                 170                 175

Trp Pro Ala His Thr Ala Val Thr Val Asp Ala Gly Gly Thr Val Thr
            180                 185                 190

Asn Phe Gln Thr Gly Asp Thr Leu Val Ala Thr Ala Asp Asp Ala Thr
        195                 200                 205

His Gln Leu Thr Val Thr Arg Asn Gly Thr Val Glu Lys Thr Phe Pro
    210                 215                 220

Met Ser Met Gly Met Thr Ala Gly Asn His Gln Thr Pro Asn Gly Thr
225                 230                 235                 240

Tyr Tyr Val Gln Asp Lys Lys Ala Ser Val Val Met Asp Ser Ser Thr
                245                 250                 255

Tyr Gly Val Pro Val Asn Ser Thr Tyr Gly Tyr Lys Val Thr Val Glu
            260                 265                 270

Asp Ala Val Arg Phe Asp Asn Val Gly Asp Tyr Val His Ser Ala Pro
        275                 280                 285

Trp Ser Val Asp Asp Gln Gly Lys Arg Asp Val Ser His Gly Cys Ile
    290                 295                 300

Asn Ile Ser Pro Ala Asn Ala Lys Trp Phe Asp Asn Phe Gly Pro
305                 310                 315                 320

Gly Asp Pro Ile Ile Val Lys Asn Ser Ser Gly Gly Asp Tyr Lys Lys
                325                 330                 335

Asn Asp Gly Ser Ala Asp Trp Met Asn
            340                 345

<210> SEQ ID NO 9
<211> LENGTH: 161
```

<212> TYPE: PRT
<213> ORGANISM: Mycobacterium avium

<400> SEQUENCE: 9

Met His Pro Ala Gly Asn Cys Arg Lys Arg Cys Glu Ser Phe Ala Val
1               5                   10                  15

Arg Arg Arg Arg Gln Phe Pro Arg Gln Ala Leu Pro Arg Ala Gly Ala
            20                  25                  30

Arg Arg Asp Ala Asp Arg Arg Val Trp Asp Asn Arg Cys Ala Met
        35                  40                  45

Arg Leu Phe Leu Gly Leu Cys Ala Leu Ala Thr Ile Gly Leu Ala
    50                  55                  60

Ala Pro Ala His Ala Asp Ile Asp Asn Asp Gln Asp Phe Leu Lys Asp
65              70                  75                  80

Leu Arg Asp Ala Gly Ile Thr Tyr Gln Asp Ala Gly Asn Ala Ile Thr
                85                  90                  95

Ile Gly Lys Ser Val Cys Glu Leu Leu Asp Asp Gly Gln Ser Asp Ala
            100                 105                 110

Lys Ile Val Thr Asp Leu Arg Asn Gln Asn Pro Ala Phe Gln Gly Ala
        115                 120                 125

Ser Ala Ala Lys Phe Thr Tyr Leu Ser Ala Ala His Tyr Cys Pro Lys
130                 135                 140

Tyr Ile Thr Gly Glu Asp Arg Gly Pro Lys Pro Glu Gly Ala Val Gly
145                 150                 155                 160

Asn

<210> SEQ ID NO 10
<211> LENGTH: 114
<212> TYPE: PRT
<213> ORGANISM: Mycobacterium avium

<400> SEQUENCE: 10

Met Lys Leu Phe Leu Ile Val Ala Gly Phe Ala Ala Val Ile Gly Leu
1               5                   10                  15

Ala Val Pro Ala Arg Ala Asp Ser Thr Asp Asp Ala Phe Val Ala Ser
            20                  25                  30

Leu Asp Lys Ala Gly Ile Lys Tyr Gly Asp Ala Asp Lys Ala Ala Gly
        35                  40                  45

Ala Gly Lys Trp Val Cys Thr Thr Leu Gln Gly Gly Lys Gln Met Ser
    50                  55                  60

Asp Val Val Ser Thr Leu Gln Ser Lys Asn Ser Asn Leu Ser Asp Asp
65                  70                  75                  80

His Ala Asn Thr Phe Ala Ala Ile Ala Val Asn Ala Tyr Cys Pro Asp
                85                  90                  95

Gln Ala Ser Ser Ile Thr Pro Ala Thr Pro Thr Asp Thr Pro Pro Ser
            100                 105                 110

Thr Ser

<210> SEQ ID NO 11
<211> LENGTH: 188
<212> TYPE: PRT
<213> ORGANISM: Mycobacterium avium

<400> SEQUENCE: 11

Met Thr Ala Val Asn Ser Val Arg Thr Phe Ser Ala Ala Ala Phe Ala
1               5                   10                  15

-continued

```
Ala Cys Phe Thr Ala Ala Ala Met Leu Ala Gly Ala Gly Thr Ala
            20              25              30

Gly Ala Ala Asp Ser Cys Pro Thr Ala Ala Pro Pro Ser Gly Gly Thr
        35              40              45

Pro Asp Trp Thr Leu Thr Gly Thr Thr Gly Ser Val Ala Val Thr Gly
    50              55              60

Ser Thr Asp Thr Ala Ala Pro Val Val Asn Val Thr Ala Pro Phe Ser
65              70              75              80

Val Thr Gln Thr Gln Val His Thr Leu Arg Ala Gly Asp Gly Pro Ala
            85              90              95

Val Pro Gly Thr Ala Arg Val Ser Val Cys Tyr Met Gly Val Asn Gly
            100             105             110

Arg Asp Gly Thr Val Phe Asp Ser Ser Tyr Gln Arg Gly Ala Pro Val
        115             120             125

Asp Phe Pro Leu Gly Gly Val Val Pro Gly Phe Gln Lys Ala Ile Ala
    130             135             140

Gly Gln Lys Val Gly Ser Thr Val Ala Val Ala Met Thr Ser Ala Asp
145             150             155             160

Gly Tyr Pro Asp Gly Gln Pro Ser Ala Gly Ile Arg Pro Gly Asp Thr
            165             170             175

Leu Val Phe Ala Ile Lys Ile Leu Gly Ala Thr Thr
            180             185
```